(12) United States Patent
Cheng et al.

(10) Patent No.: US 9,353,423 B2
(45) Date of Patent: May 31, 2016

(54) HCV GENOTYPE 6 REPLICONS

(71) Applicant: Gilead Sciences, Inc., Foster City, CA (US)

(72) Inventors: Guofeng Cheng, Foster City, CA (US); William E. Delaney, IV, Foster City, CA (US); Betty Peng, London (GB); Mei Yu, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/073,488

(22) Filed: Nov. 6, 2013

(65) Prior Publication Data

US 2014/0134604 A1 May 15, 2014

Related U.S. Application Data

(60) Provisional application No. 61/723,672, filed on Nov. 7, 2012.

(51) Int. Cl.
| | |
|---|---|
| *C12Q 1/70* | (2006.01) |
| *C07K 16/00* | (2006.01) |
| *C07K 14/005* | (2006.01) |
| *C07K 16/10* | (2006.01) |
| *C12N 7/00* | (2006.01) |

(52) U.S. Cl.
CPC .............. *C12Q 1/707* (2013.01); *C07K 14/005* (2013.01); *C07K 16/10* (2013.01); *C12N 7/00* (2013.01); *C12N 2770/24221* (2013.01); *C12N 2770/24222* (2013.01); *C12N 2770/24251* (2013.01)

(58) Field of Classification Search
None
See application file for complete search history.

(56) References Cited

U.S. PATENT DOCUMENTS

| 6,881,821 B2 * | 4/2005 | Simmonds et al. ............ 530/300 |
| 2011/0059512 A1 * | 3/2011 | Gottwein et al. .......... 435/235.1 |

FOREIGN PATENT DOCUMENTS

| WO | WO 97/40168 A1 | 10/1997 |
| WO | WO 00/66623 A2 | 11/2000 |
| WO | WO 01/89364 A2 | 11/2001 |

OTHER PUBLICATIONS

Yu et al. (Antimicrobial Agents and Chemotherapy, 2014, vol. 58, p. 2638-2646).*
Herlihy et al. (Antimicrobial Agents and Chemotherapy, 2008, vol. 52, p. 3523-3531).*
Rehmann et al. (Nature 2005, p. 215-229).*
Wong et al. (Virology, Jul. 2012, p. 57-62).*
Shimakami et al. (Journal of Virology, 2004, p. 2738-2748).*
Jones et al. (Journal of Virology, 2011, p. 12351-12361).*
Bechtel et al., "In Vitro Profiling of GSK2336805, A Potent and Selective Inhibitor of HCV NS5A," *EASL 46th Annual Meeting*, Mar. 30-Apr. 3, 2011, Berlin, Germany, XP-002720296, pp. 1-6.
Cheng et al., "Antimicrob Agents Chemother," vol. 55, pp. 2197-2205 (2011).
Gottwein et al., "Development and Characterization of Hepatitis C Virus Genotype 1-7 Cell Culture Systems: Role of CD81 and Scavenger Receptor Class B Type I and Effect of Antiviral Drugs," *Hepatology*, Feb. 2009, XP-002516448, pp. 364-377.
Jules, "Conference Reports for NATAP: In vitro profiling of GSK2336805, A Potent and Selective Inhibitor of HCV NS5A," retrieved from <http://www.natap.org/2011/EASL/EASL_74.htm>, Apr. 14, 2011.
Robinson, M. et al., "Antimicrob Agents Chemother," vol. 54, pp. 3099-3106 (2010).
International Search Report and Written Opinion, dated Mar. 3, 2014, in International Application No. PCT/US2013/068783.
Int'l Search Report—Writen Opinion dated May 21, 2015 for PCT/US2013/068783.

* cited by examiner

*Primary Examiner* — Agnieszka Boesen
(74) *Attorney, Agent, or Firm* — Yu-Ming Dammann

(57) ABSTRACT

Replicons of genotype 6 hepatitis C virus (HCV) are provided. These replicons contain adaptive mutations giving rise to the HCV's capability to replicate in vitro. Methods of preparing genotype 6 replicons and methods of using these replicons to screen antiviral agents are also provided.

17 Claims, 10 Drawing Sheets

Figure 2:
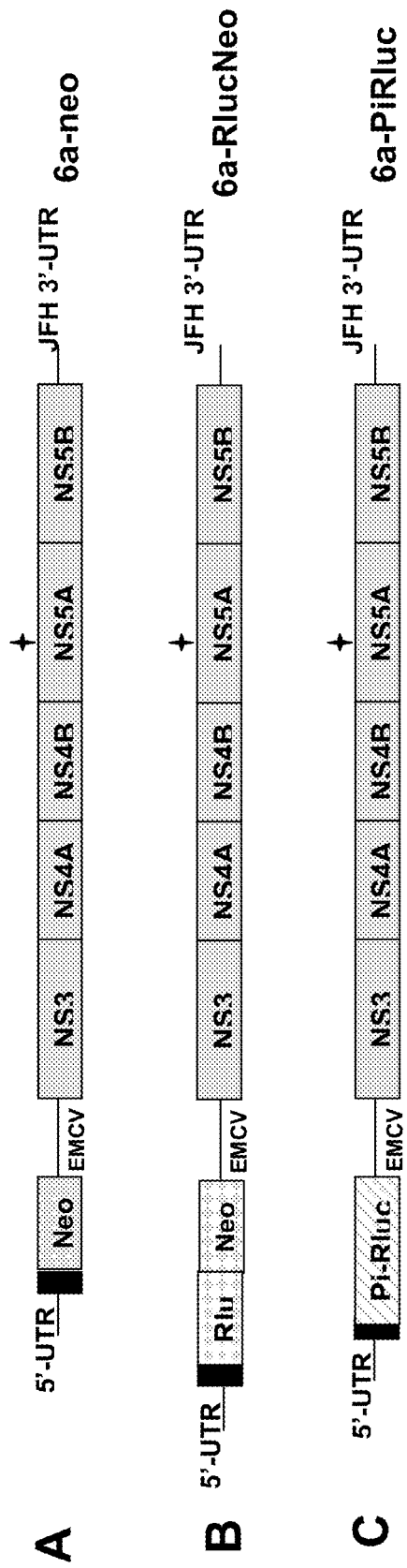

```
GCCAGCCCCTTAACGGGGCGACACTCCGCCATTATCACTCCCCTGTGAGGAACTACTGTCTTCACGCAGAAAGCGTC
TAGCCATGGCGTTAGTATCAGTGTCGTACAGCCTCCAGGCCCCCCCTCCCGGGACAGCCATAGTGGTCTGCGGAAC
CGGTGAGTACACCGGAATTGCCAGGATGACCGGGTCCTTTCCATTGGATCAAACCCGCTCAATGCCTGGAGATTTGG
GCGTGCCCCCGCAAGACTGCTAGCCGAGTAGCGTTGGGTTGCGAAAGGCCTTGTGGTACTGCCTGATAGGGTGCTTG
CGAGTGCCCCGGGAGGTCTCGTAGACCGTGCATCATGAGCACACTTCCAAAACCCCAAAGAAAAACCAAAAGAAACA
CCAACGGCGCGCCAATGATTGAACAAGATGGATTGCACGCAGGTTCTCCGGCCGCTTGGGTGGAGAGGCTATTCGGC
TATGACTGGGCACAACAGACAATCGGCTGCTCTGATGCCGCCGTGTTCCGGCTGTCAGCGCAGGGGCGCCCGGTTCT
TTTTGTCAAGACCGACCTGTCCGGTGCCCTGAATGAACTGCAGGACGAGGCAGCGCGGCTATCGTGGCTGGCCACGA
CGGGCGTTCCTTGCGCAGCTGTGCTCGACGTTGTCACTGAAGCGGGAAGGGACTGGCTGCTATTGGGCGAAGTGCCG
GGGCAGGATCTCCTGTCATCTCACCTTGCTCCTGCCGAGAAAGTATCCATCATGGCTGATGCAATGCGGCGGCTGCA
TACGCTTGATCCGGCTACCTGCCCATTCGACCACCAAGCGAAACATCGCATCGAGCGACCACGTACTCGGATGGAAG
CCGGTCTTGTCGATCAGGATGATCTGGACGAAGAGCATCAGGGGCTCGCGCCAGCCGAACTGTTCGCCAGGCTCAAG
GCGCGCATGCCCGACGGCGAGGATCTCGTCGTGACCCATGGCGATGCCTGCTTGCCGAATATCATGGTGGAAAATGG
CCGCTTTTCTGGATTCATCGACTGTGGCCGGCTGGGTGTGGCGGACCGCTATCAGGACATAGCGTTGGCTACCCGTG
ATATTGCTGAAGAGCTTGGCGGCGAATGGGCTGACCGCTTCCTCGTGCTTTACGGTATCGCCGCTCCCGATTCGCAG
CGCATCGCCTTCTATCGCCTTCTTGACGAGTTCTTCTGAGGCCGGCCGCGGCCGCAACAGACCACAACGGTTTCCCT
CTAGCGGGATCAATTCCGCCCCCCCCCCCTAACGTTACTGGCCGAAGCCGCTTGGAATAAGGCCGGTGTGCGTTGT
CTATATGTTATTTTCCACCATATTGCCGTCTTTTGGCAATGTGAGGGCCCGGAAACCTGGCCCTGTCTTCTTGACGA
GCATTCCTAGGGGTCTTTCCCCTCTCGCCAAAGGAATGCAAGGTCTGTTGAATGTCGTGAAGGAAGCAGTTCCTCTG
GAAGCTTCTTGAAGACAAACAACGTCTGTAGCGACCCTTTGCAGGCAGCGGAACCCCCCACCTGGCGACAGGTGCCT
CTGCGGCCAAAAGCCACGTGTATAAGATACACCTGCAAAGGCGGCACAACCCCAGTGCCACGTTGTGAGTTGGATAG
TTGTGGAAACAGTCAAATGGCTCTCCTCAAGCGTATTCAACAAGGGGCTGAAGGATGCCCAGAAGGTACCCCATTGT
ATGGGATCTGATCTGGGGCCTCGGTGCACATGCTTTACATGTGTTTAGTCGAGGTTAAAAAAACGTCTAGGCCCCCC
GAACCACGGGGACGTGGTTTTCCTTTGAAAAACACGATACGCGTATGGCTCCCATCACCGCGTATGCGCAGCAGACG
AGGGGCCTAGTCGGCACCATTGTGACCAGCCTAACCGGGCGTGACAAAAATGAGGTCGAAGGGGAGGTACAGGTGGT
CTCCACGGCTACCCAATCCTTCCTGGCGACCTCCATTAATGGTGTCATGTGGACTGTTTATCATGGGCCGGTTCAA
AGACTCTCGCTGGACCGAAAGGACCAGTGTGTCAAATGTACACCAATGTGGACAAGGACCTAGTAGGATGGCCATCT
CCCCCGGGAGCAAGGTCGCTCACCCCATGTACTTGTGGCTCTAGTGACCTCTATCTGGTCACGAGGGAGGCCGACGT
TATCCCCGCAAGGCGCAGGGGTGACAACCGTGCTGCCCTCCTCTCTCCTAGGCCCATAAGCACCTTGAAAGGCTCCT
CGGGAGGCCCCATTATGTGTCCCTCGGGGCACGTTGTGGGACTCTTCCGAGCTGCCGTATGCACAAGGGGTGTAGCA
AAATCCTTAGATTTTATCCCAGTGGAAAACATGGAGACGACTATGCGCTCTCCCTCATTCACAGACAACTCCACGCC
GCCTGCGGTGCCCCAGACCTATCAGGTAGGGTATCTGCACGCACCAACAGGCAGCGGAAAGAGCACCCGTGTTCCGG
CGGCGTACGCTAGCCAGGGCTACAAGGTGTTGGTCTTGAACCCATCGGTGGCGCAACGCTTAGCTTTGGCTCTTAT
ATGAGGCAAGCTTACGGCGTGGAGCCGAATGTCCGGACCGGGGTCAGGACTGTAACCACAGGGGGCGCTATCACGTA
CTCCACATATGGGAAATTCTTGGCCGATGGGGGATGTTCCGGAGGAGCGTACGACATCATCATCTGTGATGAGTGCC
ACTCCACAGACCCTACGACGGTGTTGGGCATTGGCACGGTTCTCGACCAGGCTGAGACTGCCGGGGTTCGCCTTACT
GTGCTCGCAACAGCAACGCCGCCGGGTTCTGTCACTGTCCCCATCCTAACATAACAGAGACAGCCCTCCCGACTAC
GGGAGAAATACCATTTTATGGAAAGGCCATCCCCCTTGAGTACATCAAAGGGGAAGACATCTCATATTCTGTCACT
CAAAGAAGAAGTGCGATGAGCTGGCCGGGAAACTGAAATCACTCGGCTTAAACGCCGTCGCATTCTACAGAGGTGTC
GATGTGTCCGTCATCCCCACCTCGGGCGATGTCGTCGTCTGCGCAACAGACGCCCTTATGACCGGCTACACAGGCGA
TTTCGATTCCGTCATCGACTGTAACGTAGCCGTGACACAGGTGGTGGATTTCAGCTTGGACCCAACATTTTCCATAG
AGACTACCACCGTCCCTCAGGATGCGGTATCACGGAGCCAACGACGAGGCCGCACGGGGCGGGTAAACCGGGGGTG
TACAGATTTGTCTCCCAAGGGGAGAGGCCTTCGGGTATGTTCGACACCGTCGTCCTGTGTGAGGCTTATGACACGGG
ATGCGCGTGGTACGAACTAACCCCTTCTGAAACAACTGTCAGGTTGAGGGCCTATATGAACACTCCTGGCCTTCCCG
TATGCCAAGACCACCTGGAATTTTGGGAAGGCGTGTTTACTGGCTTGACTCACATAGACGCCCACTTTCTGTCTCAG
ACGAAGCAGGGGGTGAGAACTTCGCGTACCTCGTGGCATACCAGGCTACAGTGTGCGCCAGGGCCAAAGCCCCCCC
GCCTTCTTGGGATACGATGTGGAAGTGTCTCATCAGACTCAAACCCACCCTTACCGGCCCCACTCCACTTTTGTATC
GGCTGGGGGCCGTCCAAAATGAGATAATAACAACCCATCCAATAACCAAATACATCATGACCTGTATGTCTGCGGAT
TTGGAGGTTATCACCAGCACATGGGTCCTCGTGGGTGGAGTCCTAGCCGCGCTCGCAGCCTACTGCTTGTCAGTGGG
CTGTGTTGTCATCTGTGGCAGGATAACTTTGACTGGCAAGCCTGCTGTTGTCCCTGATCGCAGATCTTATACCAGC
AATTTGACGAGATGGAGGAGTGCTCTAGGCACATCCCCTACCTCGCTGAGGGCCAGCAGATCGCCGAACAGTTCAGA
CAAAAGGTGTTGGGACTCCTCCAAGCGAGCGCTAAGCAGGCAGAAGAACTGAAGCCTGCTGTCCATTCCGCGTGGCC
TAGGGTGGAGGAGTTTTGGAGGAAACACATGTGGAACTTTGTCAGCGGGATTCAGTACTTGGCGGGCTTATCCACTC
TGCCCGGCAACCCAGCCGTGGCATCATTGATGTCATTTACAGCGTCGCTGACCAGTCCTCTGAGGACTTCTCAGA--
```

FIG. 1

```
--CCCTGCTCCTCAACATACTCGGCGGCTGGATAGCCACCCAAGTGGCTCCCCCCCCCGCGTCTACAGCTTTTGTCG
TGAGCGGTCTAGCAGGAGCCACGGTTGGAAGCATCGGGCTCGGGAGGGTGTTGGTTGATGTGCTCGCCGGATACGGA
GCCGGTGTGTCGGGTGCTCTAGTCGCTTTCAAGATCATGAGCGGCGAGTGCCCGACCACGGAAGACATGGTCAATCT
GCTACCCGCGCTGTTGTCGCCAGGGGCTCTCGTGGTGGGGGTCGTGTGTGCTGCCATCTTAAGACGCCACGTTGGCC
CTGCTGAGGGTGCTAACCAGTGGATGAACAGGCTAATAGCCTTTGCATCAAGAGGCAACCACGTGTCCCCGACGCAC
TACGTGCCTGAGACTGACGCATCAAAAAATGTGACTCAGATACTCACTTCTCTTACCATCACCAGCCTACTCCGTAG
ATTACATCAGTGGGTCAATGAAGACACGGCCACCCCTTGCGCTACCTCATGGTTACGCGACGTGTGGGACTGGGTGT
GTACAGTGTTATCTGATTTTAAAGTATGGCTGCAAGCCAAACTTCTCCCTCGCCTGCCGGGGATCCCCTTCCTCTCG
TGCCAAACGGGATATAGGGGAGTCTGGGCAGGGGACGGGGTGTGCCACACCACTTGTACCTGTGGGGCCGTGATAGC
TGGACACGTCAAAAATGGCACCATGAAAATCACAGGGCCCAAGACATGCAGTAACACTTGGCACGGGACTTTTCCAA
TCAACGCCACCACTACCGGCCCCAGCACACCACGACCAGCCCCCAACTATCAGCGCGCTCTTTGGCGGGTATCTGCC
GAGGACTACGTTGAGGTACGGAGGTTGGGCGACTGCCACTATGTGGTAGGGGTCACTGCTGAAGGGTTGAAGTGCCC
TTGCCAGGTGCCTGCGCCTGAATTCTTCACTGAGGTCGATGGCGTGAGGATACACCGTTACGCGCCACCTTGCAAGC
CCTTGCTCAGGGACGAAGTGACTTTCTCTGTGGGTCTTTCAAACTATGCCATAGGGTCGCAGCTCCCTTGCGAGCCA
GAGCCTGACGTGACCGTAGTCACCTCAATGCTCACAGACCCCACGCACATCACCGCAGAGACGGCAGCACGGCGGTT
GAAGAGGGGGTCCCCCCCTCCTTAGCCAGCTCTTCGGCCATCCAGCTGTCTGCCACCGTCCCTCAAGGCTACTTGCA
CAACTTCCAAAGACCACCCGGACATGGAACTCATCGAGGCCAACCTCCTTTGGAGGCAGGAGATGGGAGGCAACATC
ACTCGAGTCGAGTCAGAGAACAAAGTTGTAGTACTTGACTCCTTTGAGCCTCTAACCGCTGAGTATGACGAGAGGGA
AATCTCAGTATCAGCTGAGTGCCATAGGCCACCCAGGCACAAATTCCCTCCAGCTCTCCCAATATGGGCCAGGCCTG
ACTACAATCCACCTCTCCTACAAGCATGGCAAATGCCCGGATACGAGCCTCCAGTCGTGTCTGGGTGTGCCGTCGCC
CCACCTAAACCGGCACCAATTCCCCCGCCGAGGCGGAAGAGGCTAGTGCACTTGGATGAGTCCACGGTCTCGCACGC
CTTGGCGCAGCTCGCCGACAAGGTATTTGTGGAGAGTAGTAGTGACCCAGGACCTAGTTCAGACTCGGGACTATCAA
TAACCAGTCCCGTTCCACCTGCCCCAACAACACCGGACGACGCCTGCTCAGAAGCAGAGTCCTATAGCTCAATGCCC
CCTCTTGAGGGGGAGCCTGGTGACCCTGACCTAAGCTCAGGCTCTTGGTCCACTGTGAGCGATCAGGACGACGTCGT
GTGTTGTTCCATGTCCTATTCCTGGACGGGGGCTCTAATAACACCATGTGCTGCGGAGGAGGAGAAGCTTCCAATAA
ATCCCCTGAGCAACTCCCTCATAAGACACCATAACATGGTGTATTCCACCACATCACGCAGCGCCAGCCTCCGCCAG
AAGAAGGTCACATTTGACAGAGTGCAAGTGTTCGACCAACATTATCAGGATGTACTAAAGGAGATTAAGCTTCGAGC
GTCCACGGTGCAGGCGAAGCTCCTATCCATAGAGGAAGCCTGCGACCTCACACCATCGCACTCAGCCCGGTCCAAAT
ATGGGTATGGTGCACAGGACGTTAGAAGCCATGCTAGCAAGGCCGTTGACCACATCCGCTCCGTGTGGGAGGACTTG
CTAGAAGACTCTGATACCCCAATTCCCACGACCATCATGGCTAAGAATGAAGTCTTCTGCGTAGATCCGTCGAAGGG
TGGACGCAAGCCGGCACGCCTAATAGTTTACCCAGACTTGGGCGTGCGGGTCTGCGAGAAGATGGCCCTATACGACG
TGACGCGGAAGTTACCACAGGCCGTGATGGGTTCAGCATACGGATTCCAGTACTCCCCTAACCAGAGGGTTGAGTAC
TTGCTCAAAATGTGGCGGTCAAAGAAGGTGCCCATGGGCTTTCTTACGACACCAGGTGTTTTGATTCAACCGTCAC
CGAGCGGGATATCCGGACTGAGAACGACATCTATCAGTCTTGCCAGCTGGATCCCGTGGCAAGGAAGGCAGTATCAT
CCCTAACAGAACGGCTCTACGTACGCGGCCCCATGGTAAACTCCAAGGGACAGTCATGTGGCTACCGTAGATGCCGC
GCCAGTGGGGTGCTGCCCACGAGCATGGGAAACACCCTCACATGCTATCTGAAGGCACAGGCCGCCTGCAGGGCGGC
CAACATCAAGGACTGTGACATGTTGGTGTGCGGAGATGACTTAGTGGTCATTTGTGAGAGTGCTGGCGTCCAGGAGG
ACACTGCGTCACTGCGGAGCATTCACGGATGCTATGACCAGGTACTCAGCTCCCCCTGGAGACGCCCCGCAACCTACG
TATGACCTTGAGCTCATAACATCGTGCTCATCCAATGTCTCCGTCGCCCACGACGGCAATGGGAAGAGATATTACTA
CCTCACACGTGACTGTACCACTCCACTTGCGCGGGCCGCCTGGGAGACACCCGCCACACTCCAGTCAATTCGTGGT
TGGGCAACATCATTATGTTTGCCCCCACGATATGGGTGCGTATGGTTCTGATGACCCATTTTTTCTCCATCCTCCAG
TCGCAAGAACAATTGGAGAAAGCACTCGACTTTGACATCTACGAGTGACCTATTCCGTCTCTCCACTTGATCTCCC
AGCAATCATTCAACGACTCCATGGCATGGCAGCATTTTCACTCCACGGATACTCTCCAGTTGAGCTCAATAGGGTAG
GGGCTTGCCTCAGGAAACTTGGGGTACCTCCCTTGCGAGCCTGGAGACATCGAGCCAGAGCTGTCAGAGCCAAACTC
ATTGCCCAAGGGGGGAAAGCGGCTATATGCGGTAAGTACCTCTTCAACTGGGCGGTGAAGACCAAACTAAAACTCAC
TCCATTGGTCTCCGCGAGCAAGCTTGACTTATCAGGCTGGTTCGTGGCAGGCTACGACGGGGGGGACATTTATCACA
GCGTGTCCCAGGCTCGACCCCGTCTCTTACTCCTTGGCCTACTCCTACTCACCGTAGGGGTAGGCATCTTTTTGCTC
CCCGCTCGGTAGAGCGGCACACACTAGGTACACTCCATAGCTAACTGTTCCTTTTTTTTTTTTTTTTTTTTTTTTTT
TTTTTTTTTTTTTTTCTTTTTTTTTTTTTCCCTCTTTCTTCCCTTCTCATCTTATTCTACTTTCTTTCTTGGTG
GCTCCATCTTAGCCCTAGTCACGGCTAGCTGTGAAAGGTCCGTGAGCCGCATGACTGCAGAGAGTGCCGTAACTGGT
CTCTCTGCAGATCATGT
```

FIG. 1 (cont'd)

FIG. 9

```
                     SEQUENCE LISTING

<160> NUMBER OF SEQ ID NOS: 8

<210> SEQ ID NO 1
<211> LENGTH: 8021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gccagcccct taacggggcg acactccgcc attatcactc ccctgtgagg aactactgtc      60
ttcacgcaga aagcgtctag ccatggcgtt agtatgagtg tcgtacagcc tccaggcccc     120
cccctcccgg gagagccata gtggtctgcg gaaccggtga gtacaccgga attgccagga     180
tgaccgggtc ctttccattg gatcaaaccc gctcaatgcc tggagatttg ggcgtgcccc     240
cgcaagactg ctagccgagt agcgttgggt tgcgaaaggc cttgtggtac tgcctgatag     300
ggtgcttgcg agtgccccgg gaggtctcgt agaccgtgca tcatgagcac acttccaaaa     360
ccccaaagaa aaaccaaaag aaacaccaac ggcgcgccaa tgattgaaca agatggattg     420
cacgcaggtt ctccggccgc ttgggtggag aggctattcg gctatgactg ggcacaacag     480
acaatcggct gctctgatgc cgccgtgttc cggctgtcag cgcaggggcg cccggttctt     540
tttgtcaaga ccgacctgtc cggtgccctg aatgaactgc aggacgaggc agcgcggcta     600
tcgtggctgg ccacgacggg cgttccttgc gcagctgtgc tcgacgttgt cactgaagcg     660
ggaagggact ggctgctatt gggcgaagtg ccggggcagg atctcctgtc atctcacctt     720
```

```
gctcctgccg agaaagtatc catcatggct gatgcaatgc ggcggctgca tacgcttgat    780
ccggctacct gcccattcga ccaccaagcg aaacatcgca tcgagcgagc acgtactcgg    840
atggaagccg gtcttgtcga tcaggatgat ctggacgaag agcatcaggg gctcgcgcca    900
gccgaactgt tcgccaggct caaggcgcgc atgcccgacg gcgaggatct cgtcgtgacc    960
catggcgatg cctgcttgcc gaatatcatg gtggaaaatg gccgcttttc tggattcatc   1020
gactgtggcc ggctgggtgt ggcggaccgc tatcaggaca tagcgttggc tacccgtgat   1080
attgctgaag agcttggcgg cgaatgggct gaccgcttcc tcgtgcttta cggtatcgcc   1140
gctcccgatt cgcagcgcat cgccttctat cgccttcttg acgagttctt ctgaggccgg   1200
ccgcggccgc aacagaccac aacggtttcc ctctagcggg atcaattccg cccccccccc   1260
ctaacgttac tggccgaagc cgcttggaat aaggccggtg tgcgtttgtc tatatgttat   1320
tttccaccat attgccgtct tttggcaatg tgagggcccg gaaacctggc cctgtcttct   1380
tgacgagcat tcctagggt ctttcccctc tcgccaaagg aatgcaaggt ctgttgaatg   1440
tcgtgaagga agcagttcct ctggaagctt cttgaagaca acaacgtct gtagcgaccc    1500 tttgcaggca gcggaacccc ccacctggcg acaggtgcct ctgcggccaa aagccacgtg   1560
tataagatac acctgcaaag gcggcacaac cccagtgcca cgttgtgagt tggatagttg   1620
tggaaagagt caaatggctc tcctcaagcg tattcaacaa ggggctgaag gatgcccaga   1680
aggtacccca ttgtatggga tctgatctgg ggcctcggtg cacatgcttt acatgtgttt   1740
agtcgaggtt aaaaaaacgt ctaggccccc cgaaccacgg ggacgtggtt ttcctttgaa   1800
aaacacgata cgcgtatggc tcccatcacc gcgtatgcgc agcagacgag gggcctagtc   1860
ggcaccattg tgaccagcct aaccgggcgt gacaaaaatg aggtcgaagg ggaggtacag   1920
gtggtctcca cggctaccca atccttcctg gcgacctcca ttaatggtgt catgtggact   1980
gtttatcatg gggccggttc aaagactctc gctggaccga aaggaccagt gtgtcaaatg   2040
tacaccaatg tggacaagga cctagtagga tggccatctc ccccgggagc aaggtcgctc   2100
accccatgta cttgtggctc tagtgacctc tatctggtca cgagggaggc cgacgttatc   2160
cccgcaaggc gcaggggtga caaccgtgct gccctcctct ctcctaggcc cataagcacc   2220
ttgaaaggct cctcgggagg ccccattatg tgtccctcgg ggcacgttgt gggactcttc   2280
cgagctgccg tatgcacaag gggtgtagca aaatccttag attttatccc agtggaaaac   2340
atggagacga ctatgcgctc tccctcattc acagacaact ccacgccgcc tgcggtgccc   2400
cagacctatc aggtagggta tctgcacgca ccaacaggca gcggaaagag cacccgtgtt   2460
ccggcggcgt acgctagcca gggctacaag gtgttggtct tgaacccatc ggtggcggca   2520
acgcttagct ttggctctta tatgaggcaa gcttacggcg tggagccgaa tgtccggacc   2580
ggggtcagga ctgtaaccac aggggggcgct atcacgtact ccacatatgg gaaattcttg   2640
gccgatgggg gatgttccgg aggagcgtac gacatcatca tctgtgatga gtgccactcc   2700
acagacccta cgacggtgtt gggcattggc acggttctcg accaggctga gactgccggg   2760
gttcgcctta ctgtgctcgc aacagcaacg ccgccgggtt ctgtcactgt cccccatcct   2820
aacataacag agacagccct cccgactacg ggagaaatac cattttatgg aaaggccatc   2880 cccttgagt acatcaaagg gggaagacat ctcatattct gtcactcaaa aagaagtgc   2940 gatgagctgg ccgggaaact gaaatcactc ggcttaaacg ccgtcgcatt ctacagaggt   3000
gtcgatgtgt ccgtcatccc cacctcgggc gatgtcgtcg tctgcgcaac agacgccctt   3060
atgaccggct acacaggcga tttcgattcc gtcatcgact gtaacgtagc cgtgacacag   3120
```

```
gtggtggatt tcagcttgga cccaacattt tccatagaga ctaccaccgt ccctcaggat    3180
gcggtatcac ggagccaacg acgaggccgc acggggcggg gtaaaccggg ggtgtacaga    3240
tttgtctccc aaggggagag gccttcgggt atgttcgaca ccgtcgtcct gtgtgaggct    3300
tatgacacgg gatgcgcgtg gtacgaacta accccttctg aaacaactgt caggttgagg    3360
gcctatatga acactcctgg ccttcccgta tgccaagacc acctggaatt ttgggaaggc    3420
gtgtttactg gcttgactca catagacgcc cactttctgt ctcagacgaa gcagggggt    3480 gagaacttcg cgtacctcgt ggcataccag gctacagtgt gcgccagggc caaagccccc    3540
ccgccttctt gggatacgat gtggaagtgt ctcatcagac tcaaacccac ccttaccggc    3600
cccactccac ttttgtatcg gctggggggcc gtccaaaatg agataataac aacccatcca    3660
ataaccaaat acatcatgac ctgtatgtct gcggatttgg aggttatcac cagcacatgg    3720
gtcctcgtgg gtggagtcct agccgcgctc gcagcctact gcttgtcagt gggctgtgtt    3780
gtcatctgtg gcaggataac tttgactggc aagcctgctg ttgtccctga tcgcgagatc    3840
ttataccagc aatttgacga gatggaggag tgctctaggc acatcccta cctcgctgag    3900 ggccagcaga tcgccgaaca gttcagacaa aaggtgttgg gactcctcca agcgagcgct    3960
aagcaggcag aagaactgaa gcctgctgtc cattccgcgt ggcctagggt ggaggagttt    4020
tggaggaaac acatgtggaa cttttgtcagc gggattcagt acttggcggg cttatccact    4080
ctgcccggca acccagccgt ggcatcattg atgtcattta cagcgtcgct gaccagtcct    4140
ctgaggactt ctcagaccct gctcctcaac atactcggcg gctggatagc cacccaagtg    4200
gctccccccc ccgcgtctac agcttttgtc gtgagcggtc tagcaggagc cacggttgga    4260
agcatcgggc tcgggagggt gttggttgat gtgctcgccg atacggagc cggtgtgtcg    4320 ggtgctctag tcgctttcaa gatcatgagc ggcgagtgcc cgaccacgga agacatggtc    4380
aatctgctac ccgcgctgtt gtcgccaggg gctctcgtgg tgggggtcgt gtgtgctgcc    4440
atcttaagac gccacgttgg ccctgctgag ggtgctaacc agtggatgaa caggctaata    4500
gcctttgcat caagaggcaa ccacgtgtcc ccgacgcact acgtgcctga gactgacgca    4560
tcaaaaaatg tgactcagat actcacttct cttaccatca ccagcctact ccgtagatta    4620
catcagtggg tcaatgaaga cacggccacc ccttgcgcta cctcatggtt acgcgacgtg    4680
tgggactggg tgtgtacagt gttatctgat tttaaagtat ggctgcaagc caaacttctc    4740
cctcgcctgc cggggatccc cttcctctcg tgccaaacgg gatataggg agtctgggca    4800 gggacgggg tgtgccacac cacttgtacc tgtgggccg tgatagctgg acacgtcaaa    4860
aatggcacca tgaaaatcac agggcccaag acatgcagta acacttggca cgggacttt    4920 ccaatcaacg ccaccactac cggccccagc acaccgcgac cagcccccaa ctatcagcgc    4980 gctcttttggc gggtatctgc cgaggactac gttgaggtac ggaggttggg cgactgccac    5040
tatgtggtag gggtcactgc tgaagggttg aagtgccctt gccaggtgcc tgcgcctgaa    5100
ttcttcactg aggtcgatgg cgtgaggata caccgttacg cgccaccttg caagcccttg    5160
ctcagggacg aagtgacttt ctctgtgggt cttttcaaact atgccatagg gtcgcagctc    5220
ccttgcgagc cagagcctga cgtgaccgta gtcacctcaa tgctcacaga ccccacgcac    5280
atcaccgcag agacggcagc acggcggttg aagaggggg cccccccctc cttagccagc    5340
tcttcggcca tccagctgtc tgcaccgtcc ctcaaggcta cttgcacaac ttccaaagac    5400 caccccggaca tggaactcat cgaggccaac ctcctttgga ggcaggagat gggaggcaac    5460
```

```
atcactcgag tcgagtcaga gaacaaagtt gtagtacttg actcctttga gcctctaacc    5520
gctgagtatg acgagaggga aatctcagta tcagctgagt gccataggcc acccaggcac    5580
aaattccctc cagctctccc aatatgggcc aggcctgact acaatccacc tctcctacaa    5640
gcatggcaaa tgcccggata cgagcctcca gtcgtgtctg ggtgtgccgt cgccccacct    5700
aaaccggcac caattccccc gccgaggcgg aagaggctag tgcacttgga tgagtccacg    5760
gtctcgcacg ccttggcgca gctcgccgac aaggtatttg tggagagtag tagtgaccca    5820
ggacctagtt cagactcggg actatcaata accagtcccg ttccacctgc cccaacaaca    5880
ccggacgacg cctgctcaga agcagagtcc tatagctcaa tgcccctct tgaggggag     5940 cctggtgacc ctgacctaag ctcaggctct tggtccactg tgagcgatca ggacgacgtc    6000
gtgtgttgtt ccatgtccta ttcctggacg ggggctctaa taacaccatg tgctgcggag    6060
gaggagaagc ttccaataaa tcccctgagc aactccctca taagacacca taacatggtg    6120
tattccacca catcacgcag cgccagcctc cgccagaaga aggtcacatt tgacagagtg    6180
caagtgttcg accaacatta tcaggatgta ctaaaggaga ttaagcttcg agcgtccacg    6240
gtgcaggcga agctcctatc catagaggaa gcctgcgacc tcacaccatc gcactcagcc    6300
cggtccaaat atgggtatgg tgcacaggac gttagaagcc atgctagcaa ggccgttgac    6360
cacatccgct ccgtgtggga ggacttgcta gaagactctg atacccccaat tcccacgacc    6420 atcatggcta agaatgaagt cttctgcgta gatccgtcga agggtggacg caagccggca    6480
cgcctaatag tttacccaga cttgggcgtg cgggtctgcg agaagatggc cctatacgac    6540
gtgacgcgga agttaccaca ggccgtgatg ggttcagcat acggattcca gtactcccct    6600
aaccagaggg ttgagtactt gctcaaaatg tggcggtcaa agaaggtgcc catgggcttt    6660
tcttacgaca ccaggtgttt tgattcaacc gtcaccgagc gggatatccg gactgagaac    6720
gacatctatc agtcttgcca gctggatccc gtggcaagga aggcagtatc atccctaaca    6780
gaacggctct acgtaggcgg ccccatggta aactccaagg acagtcatg tggctaccgt    6840 agatgccgcg ccagtggggt gctgcccacg agcatgggaa acaccctcac atgctatctg    6900
aaggcacagg ccgcctgcag ggcggccaac atcaaggact gtgacatgtt ggtgtgcgga    6960
gatgacttag tggtcatttg tgagagtgct ggcgtccagg aggacactgc gtcactgcga    7020
gcattcacgg atgctatgac caggtactca gctccccctg gagacgcccc gcaacctacg    7080
tatgaccttg agctcataac atcgtgctca tccaatgtct ccgtcgccca cgacggcaat    7140
gggaagagat attactacct cacacgtgac tgtaccactc cacttgcgcg ggccgcctgg    7200
gagacagccc gccacactcc agtcaattcg tggttgggca acatcattat gtttgccccc    7260
acgatatggg tgcgtatggt tctgatgacc cattttttct ccatcctcca gtcgcaagaa    7320
caattggaga aagcactcga ctttgacatc tacggagtga cctattccgt ctctccactt    7380
gatctcccag caatcattca acgactccat ggcatggcag catttcact ccacggatac    7440 tctccagttg agctcaatag ggtaggggct tgcctcagga aacttgggt acctcccttg    7500 cgagcctgga gacatcgagc cagagctgtc agagccaaac tcattgccca agggggaaa    7560 gcggctatat gcgtaagta cctcttcaac tgggcggtga agaccaaact aaaactcact    7620
ccattggtct ccgcgagcaa gcttgactta tcaggctggt tcgtggcagg ctacgacggg    7680
ggggacattt atcacagcgt gtcccaggct cgaccccgtc tcttactcct tggcctactc    7740
ctactcaccg taggggtagg catctttttg ctccccgctc ggtagagcgg cacacactag    7800
gtacactcca tagctaactg ttcctttttt tttttttttt ttttttttt ttttttttt     7860
```

```
tttttttctt ttttttttt ttccctcttt cttcccttct catcttattc tactttcttt      7920
cttggtggct ccatcttagc cctagtcacg gctagctgtg aaaggtccgt gagccgcatg      7980
actgcagaga gtgccgtaac tggtctctct gcagatcatg t                         8021
```

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

```
ggcgcgccca                                                            10
```

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
ggccggcca                                                              9
```

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
acgcgtatg                                                              9
```

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
aacaccatcg gcgcgcccat ggcttccaag gtgtacgac                            39
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tcggggccat acgcgtatcg tgttttctcaa agg                                 33
```

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 7
aacaccatcg gcgcgccaaa ccaagttcaa tag 33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tcggggccat acgcgtatcg tgtttttcaa agg 33

HCV GENOTYPE 6 REPLICONS

CROSS-REFERENCES TO RELATED APPLICATIONS

This application claims priority to U.S. Provisional Application No. 61/723,672, filed on Nov. 7, 2012, which is incorporated in its entirety herein for all purposes.

SEQUENCE LISTING

The instant application contains a Sequence Listing which has been submitted electronically in ASCII format and is hereby incorporated by reference in its entirety. Said ASCII copy, created on Dec. 31, 2013, is named 37JD-192989-US_SL.txt and is 12,522 bytes in size.

FIELD OF THE DISCLOSURE

The disclosure is directed to hepatitis C replicons of genotype 6 and methods of preparing and using the replicons.

STATE OF THE ART

Chronic hepatitis C virus (HCV) infection remains a significant global heath burden with an estimated 160 million people infected world wide. The current standard of care is 24 to 48 week courses of pegylated interferon (PegIFN) plus ribavirin (RBV). Due to the partial efficacy and poor tolerability of this regimen, the discovery and development of new antiviral agents has been intensely pursued. Recently, these efforts have culminated in the FDA approval of two NS3 protease inhibitors (boceprevir and telaprevir) for use in combination with pegylated interferon and ribavirin for the treatment of chronic genotype 1 HCV infection. Many other inhibitors are in advanced clinical development, however, the majority are being developed to treat genotype 1 infections.

HCV is a positive-strand RNA virus that exhibits extraordinary genetic diversity. Six major genotypes (i.e. genotype 1-6) along with multiple subtypes (e.g. genotype 1a, 1b, 1c etc.) have been reported. Genotypes 1, 2 and 3 have worldwide distributions. Genotypes 1a or 1b are generally predominant in North America, South America, Europe and Asia. However, genotypes 2 and 3 are common and can constitute 20 to 50% of infections in many of these areas. Genotype 4a is the predominant in the Middle East and many African countries; up to 15% of the population of Egypt is infected with HCV and 93% of infections are genotype 4. Genotype 5 is prevalent in South Africa, while Genotype 6 is most common in Asia. Although most continents and countries have a "dominant" genotype, infected populations are almost universally made up of a mixture of multiple genotypes. Furthermore, the geographical distribution and diversity (epidemiology) of HCV infection is continuously evolving, due to large-scale immigration and widespread intravenous drug use. For instance, genotype 4a has noticeably spread into central and northern Europe. This presents a clinical challenge, since it is well documented that individual genotypes respond differently to both direct antivirals and immunomodulatory therapies, including the current standard of care.

HCV replicons are self-replicating RNA sequences derived from the HCV genome and have served as workhorses both for molecular virology studies and drug discovery. To date, replicons have been established from two genotypes and three subtypes (genotypes 1a, 1b and 2a). These replicons have been crucial in multiple aspects of drug discovery and development including the identification of novel inhibitor classes, the optimization of clinical candidates and the characterization of clinical resistance. Recently, there has been increasing interest in developing next-generation drugs that are active against all major HCV genotypes. Ideally, the approval of "pan-genotypic" drugs and regimens will greatly simplify the treatment of HCV.

Genotype 6 represents a significant portion of the global unmet medical need associated with chronic HCV infection, due to the high HCV disease burden in Southeast Asia and Southern China (more than 32 million people infected). Furthermore, in contrast to North America and Europe, new incidence of HCV infection also remains high in these regions due to higher risk of exposure to contaminated blood products and intravenous drug use.

Currently, the standard treatment for HCV genotype 6 patients remains PegIFN and RBV for 24 to 48 weeks. Although genotype 6 infection is more responsive to PegIFN/RBV than genotype 1 (sustained virologic response 86% and 52%, respectively, the current standard care is still partially efficacious and is contra-indicated in many patients. No direct-acting antivirals (DAAs; i.e. neither boceprevir nor telaprevir) have been approved to treat genotype 6 HCV infection. Many HCV DAAs are in advanced clinical development, but few are being developed to treat genotype 6 infections.

Genotype 6 is the most genetically diverse HCV genotype, with at least 23 subtypes confirmed currently and new subtypes expected to be identified continuously. It is well documented that individual HCV genotypes respond differently to direct-acting antivirals due to high HCV genetic diversity among and within genotypes. For example, essentially all HCV NS3 protease inhibitors including telaprevir, though potent against genotype 1, have significantly reduced antiviral activity against genotype 3 due to the Q168 polymorphism in NS3. For NS5A inhibitors, first-generation compounds often inhibits genotype 2a JFH-1 virus efficiently but have much weaker potency (>200-fold) against major genotype 2 viral populations encoding the M31 polymorphism in NS5A. The extreme genetic diversity of genotype 6 combined with a limited virological characterization compared to common genotype 1 strains, create significant challenges to DAA development against this genotype. Meeting this challenge will require the establishment of efficient genotype 6 tools for the identification and development of new therapies.

A key step in the pursuit of pan-genotypic treatment regimens will be the development of in vitro tools that allow the study of all major genotypes and subtypes. Replicons derived from sequences of additional major genotypes (i.e. those other than genotype 1a, 1b or 2a), however, have not been generated. In particular, despite the worldwide prevalence of genotype (GT) 6 Hepatitis C virus (HCV), in particular in Southeast Asia and Southern China where it can constitute up to 50% of HCV infections, no direct-acting antivirals are approved to treat this genotype and no full-genome GT6 HCV replicons have been described.

SUMMARY

It has been discovered that clonal cell lines stably replicating Genotype 6 replicons were obtained by transcribing and electroporating subgenomic genotype 6 cDNAs into HCV permissive cell lines. Adaptive mutations have been identified from these clones, as compared to the wildtype virus. When these mutations were engineered by site-directed mutagenesis and introduced into the cell lines, HCV genotype 6 replications ensued.

These adaptive mutations for genotype 6 included S232I in NS5A, K272R in NS3 and K34R in NS4A. The establishment of robust genotype 6 replicon systems provides powerful tools to facilitate drug discovery and development efforts.

Accordingly, one embodiment of the present disclosure provides a genotype 6 hepatitis C viral (HCV) RNA construct that is capable of replication in a eukaryotic cell, wherein the RNA sequence comprises a 5'UTR, sequences encoding one or more of NS3, NS4A, NS4B, NS5A or NS5B, and a 3'UTR.

In some aspects, the construct includes a mutation in NS5A that is an isoleucine at residue 232. In some aspects, the construct include, alternatively or in addition to the S232I mutation, a mutation to arginine at residue 272 in NS3, and/or a mutation to arginine at residue 34 in NS4A. In some aspects, the construct is a subgenomic or full-length HCV replicon.

Moreover, DNA that transcribes to the RNA construct, viral particles that include the RNA construct, and cells containing such DNA or RNA are also provided. In one aspect, the construct comprises the nucleic acid sequence of SEQ ID NO: 1 of a nucleic acid sequence that has at least about 75%, 80%, 85%, 90%, 95%, 98% or 99% sequence identity to SEQ ID NO: 1, wherein the polynucleotide further comprises one or more substitutions to encode for one or more of the adaptive mutations. Further provided are polynucleotide primers, probes or amplification products that specifically hybridize to the construct or the DNA encoding it, with the adaptive mutations, wherein the primers, probes or amplification products are at least 15 nucleotides long.

Also provided, in one embodiment, are individual NS3, NS4A or NS5A proteins that include one or more of the corresponding adaptive mutations. Polynucleotides encoding these proteins and antibodies that specifically recognize the proteins are also provided.

In another embodiment, the present disclosure provides an isolated cell comprising a genotype 6 hepatitis C viral (HCV) RNA that replicates in the cell. In one aspect, there is an absence, in the cell, of a DNA construct encoding the RNA. In another aspect, the cell comprises at least 10 copies, or alternatively at least about 100, 500, 1000, 2000, 5000, 10,000, $1\times10^5$, $1\times10^6$, $1\times10^7$, $1\times10^8$ or $1\times10^9$ copies of the RNA. In any of such aspects, the RNA can be a subgenomic HCV sequence or a full-length HCV sequence and can include one or more of the adaptive mutations described above.

In one aspect, the cell is a mammalian cell which can be, for instance, a hepatoma cell, in particular a Huh7 1C cell.

Methods of improving the capability of a genotype 6 HCV viral RNA to replicate in a eukaryotic cell are also provided, comprising one or more of (a) substituting residue 232 of NS5A with an isoleucine, (b) substituting residue 272 of NS3 with an arginine, or (c) substituting residue 34 of NS4A, with an arginine.

Still provided, in one embodiment, is a method of identifying an agent that inhibits the replication or activity of a genotype 6 HCV, comprising contacting a cell of any of the above embodiments with a candidate agent, wherein a decrease of replication or a decrease of the activity of a protein encoded by the RNA indicates that the agent inhibits the replication or activity of the HCV. Alternatively, the method comprises contacting the lysate of a cell of any of the above embodiments with a candidate agent, wherein a decrease of the activity of a protein encoded by the RNA indicates that the agent inhibits the activity of the HCV.

BRIEF DESCRIPTION OF THE DRAWINGS

The disclosure is best understood from the following detailed description when read in conjunction with the accompanying drawings. Included in the drawings are the following figures:

FIG. 1 shows the nucleotide (nt) sequence of genotype 6a subgenomic replicons (8021 base pairs, SEQ ID NO: 1). The replicon sequence is based on the consensus sequence of sixteen genotype 6a genomes (Table 1) available in the European HCV database. This replicon contains the following 12 elements: 1) GT6a 5'-UTR: 1-342 nt; 2) GT6a the first 48 nucleotides of core: 343-390 nt; 3) an AscI linker: 391-399 nt; 4) the neomycin phosphotransferase II (neo) gene: 400-1194 nt; 5) an FseI linker: 1195-1212 nt; 6) the encephalomyocarditis virus (EMCV) IRES: 1213-1815 nt; 7) GT6a NS3: 1816-3711 nt; 8) GT6a NS4A: 3712-3873 nt; 9) GT6a NS4B: 3874-4656 nt; 10) GT6a NS5A: 4657-6009 nt; 11) GT6a NS5B: 6010-7782 nt; and 12) GT2a JFH-1 3'-UTR: 7783-8021.

FIG. 2A-C present schematic diagrams of genotype 6a replicon constructs. Genotype 6a subgenomic replicons encode a neomycin phosphotransferase II gene (neo) (A), a Renilla luciferase (Rluc)-neo fusion reporter (B) or a poliovirus IRES (PI)-driven Rluc reporter (C). The synthesized neo replicon incorporated following elements from 5' to 3': the GT6a 5'-UTR; the Neo reporter gene; the EMCV IRES; the NS3-NS5B polyprotein region of GT6a consensus sequence including an NS5A mutation (S232I); and the 3'-UTR of GT2a JFH. Solid dark boxes indicate GT6a core sequence. Shaded boxes indicate HCV polyprotein sequence. Crosses indicate the S232I mutation in NS5A. The 5' and 3' untranslated regions (UTR), and EMCV IRES are indicated.

FIG. 3 illustrates the strategy for novel replicon isolation.

FIG. 4 presents a chart showing stable colony formation of genotype 6a replicons requires NS5A mutation S232I.

FIG. 5 presents a chart showing high NS3 protease activity in GT6a replicon cells.

FIG. 6 presents images showing high NS5A Expression in GT6a replicon cells.

FIG. 7 includes images showing NS3 and NS4A mutations enhanced GT6a replicon replication.

FIG. 8 shows that NS3 and NS4A mutations conferred high GT6a HCV replication and 1C are more permissive than Lunet cells.

FIG. 9 shows that NS3 and NS4A adaptive mutations require the NS5A mutation S232I to confer efficient GT6a HCV replication.

DETAILED DESCRIPTION

Prior to describing this disclosure in greater detail, the following terms will first be defined.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a thread" includes a plurality of threads.

1. DEFINITIONS

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

| 1-Letter | 3-Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention. In one embodiment, the homologous peptide is one that shares the same functional characteristics as those described, including one or more of the adaptive mutations.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Jul. 15, 2011. Biologically equivalent polynucleotides are those having the specified percent homology and encoding a polypeptide having the same or similar biological activity.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells, or alternatively from a prokaryotic cells as described above. Non-limiting examples include simian, bovine, porcine, murine, rats, avian, reptilian and human.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. The antibodies can be polyclonal or monoclonal and can be isolated from any suitable biological source, e.g., murine, rat, sheep and canine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "isolated" as used herein refers to molecules or biological or cellular materials being substantially free from other materials or when referring to proteins or polynucleotides, infers the breaking of covalent bonds to remove the protein or polynucleotide from its native environment. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. The term "isolated" is also used herein to refer to cells or tissues that are isolated from other cells or tissues and is meant to encompass both cultured and engineered cells or tissues.

Hepatitis C virus or "HCV" is a small (55-65 nm in size), enveloped, positive-sense single-stranded RNA virus of the family Flaviviridae. Hepatitis C virus is the cause of hepatitis C in humans. The hepatitis C virus particle consists of a core of genetic material (RNA), surrounded by an icosahedral protective shell of protein, and further encased in a lipid (fatty) envelope of cellular origin. Two viral envelope glycoproteins, E1 and E2, are embedded in the lipid envelope.

Hepatitis C virus has a positive sense single-stranded RNA genome. The genome consists of a single open reading frame that is 9600 nucleotide bases long. This single open reading frame is translated to produce a single protein product, which is then further processed to produce smaller active proteins.

At the 5' and 3' ends of the RNA are the UTR, that are not translated into proteins but are important to translation and replication of the viral RNA. The 5' UTR has a ribosome binding site (IRES—Internal ribosome entry site) that starts the translation of a very long protein containing about 3,000 amino acids. This large pre-protein is later cut by cellular and viral proteases into the 10 smaller proteins that allow viral replication within the host cell, or assemble into the mature viral particles.

Structural proteins made by the hepatitis C virus include Core protein, E1 and E2; nonstructural proteins include NS2, NS3, NS4, NS4A, NS4B, NS5, NS5A, and NS5B.

Based on genetic differences between HCV isolates, the hepatitis C virus species is classified into six genotypes (1-6) with several subtypes within each genotype (represented by letters). Subtypes are further broken down into quasispecies based on their genetic diversity. The preponderance and distribution of HCV genotypes varies globally. For example, in North America, genotype 1a predominates followed by 1b, 2a, 2b, and 3a. In Europe, genotype 1b is predominant followed by 2a, 2b, 2c, and 3a. Genotypes 4 and 5 are found almost exclusively in Africa. While genotype 6 is found predominately in Southeast Asia. Genotyping is clinically important in determining potential response to interferon-based therapy and the required duration of such therapy. Genotypes 1 and 4 are less responsive to interferon-based treatment than are the other genotypes (2, 3, 5 and 6). Duration of standard interferon-based therapy for genotypes 1 and 4 is 48 weeks, whereas treatment for genotypes 2 and 3 is completed in 24 weeks.

Sequences from different HCV genotypes can vary as much as 33% over the whole viral genome and the sequence variability is distributed equally throughout the viral genome, apart from the highly conserved 5' UTR and core regions and the hypervariable envelope (E) region.

HCV genotypes can be identified with various methods known in the art. PCR-based genotyping with genotype-specific primers was first introduced in 1992, in particular with primers targeting the core region. Commercial kits (e.g., InnoLipa® by Innogenetics (Zwijindre, Belgium)) are also available. Direct sequencing, in the vein, can be used for more reliable and sensitive genotyping.

Serologic genotyping uses genotype-specific antibodies and identifies genotypes indirectly. Two commercially available serologic genotyping assays have been introduced, including a RIBA SIA assay from Chiron Corp. and the Murex HCV serotyping enzyme immune assay from Nurex Diagnostics Ltd.

Sequences of genotype 6 HCV have been identified. For instance, GenBank accession # NC 009827 represents a genomic sequence. Further discussion of the genotype 6 and their sequences are clinical impacts can be found at Pang P S, Planet P J, Glenn J S (2009) PLoS ONE 4(8): e6579.doi: 10.1371/journal.pone.0006579.

The term "replicon" refers to a DNA molecule or RNA molecule, or a region of DNA or RNA, that replicates from a single origin of replication. For most prokaryotic chromosomes, the replicon is the entire chromosome. In some aspects, a replicon refers to a DNA or RNA construct that replicates in a cell in vitro. In one aspect, a replicon can replicate to produce at least about 10, or alternatively, at least about 100, 500, 1000, 2000, 5000, 10,000, $1\times10^5$, $1\times10^6$, $1\times10^7$, $1\times10^8$ or $1\times10^9$ copies of the replicon in a cell in vitro. Alternatively, a replicon's replication efficiency can be measured by producing certain amount of viral RNA in total RNA that includes cellular RNA. In one aspect, a replicon can produce at least about 1000, $1\times10^4$, $1\times10^5$, $1\times10^6$, $1\times10^7$, $1\times10^8$, $1\times10^9$, $1\times10^{10}$, $1\times10^{11}$, or $1\times10^{12}$ copies of the replicon per microgram of total RNA or cellular RNA.

A "subgenomic" HCV sequence refers to a HCV sequence that does not include all sequences of a wild-type HCV. In one aspect, a subgenomic HCV or a subgenomic HCV replicon does not include the E1, E2 or C regions. In another aspect, a subgenomic HCV or a subgenomic HCV replicon includes all or part of the 5' UTR, NS3, NS4A, NS4B, NS5A, NS5B and 3' UTR sequences. In contrast, a "full-length" or "full genome" HCV or HCV replicon includes E1, E2 and C regions. In some aspects, both a subgenomic and a full-length HCV replicon can include one or more of a reporter gene (e.g., luciferase), a marker gene (e.g., Neo), and an IRES (e.g., EMCV IRES) sequence.

A virus particle (or virion) consists of the genetic material made from either DNA or RNA of a virus and a protein coat that protects the genetic material. In one aspect, an envelope of lipids surrounds the protein coat when they are outside a cell.

The term "adaptive mutation" of a HCV replicon of a certain genotype refers to a mutation, as compared to a wild-type HCV sequence of the genotype, that enables the wild-type replicon to replicate in a cell, in particular in a eukaryotic cell such as a mammalian cell and in vitro, or enhances a HCV replicon's ability to replicate. It is contemplated that an adaptive mutation can favorably influence assembly of the replicase complex with host cell-specific protein, or alternatively promote interactions of the protein that includes the adaptive mutation (e.g., NS3, NS4A, NS4B, NS5A etc) with cellular proteins involved in host cell antiviral defenses.

A "reporter gene" refers to a gene that can be attached to a regulatory sequence of another gene of interest in cell culture, animals or plants, to facilitate identification of this other gene. Reporter genes are often used as an indication of whether a certain gene has been taken up by or expressed in the cell or organism population. Non-limiting examples of reporter gene include the luciferase gene and the green fluorescent protein gene.

A "marker gene" or "selectable marker" refers to a gene that protects the organism from a selective agent that would normally kill it or prevent its growth. One non-limiting example is the neomycin phosphotransferase gene (Neo), which upon expression confers resistance to G418, an aminoglycoside antibiotic similar in structure to gentamicin B1.

HCV Genotype 6 Replicon Constructs

The present disclosure relates, in general, to the unexpected discovery that clonal cell lines stably replicating genotype 6 replicons can be obtained by transcribing and electroporating subgenomic genotype 6 cDNAs into HCV permissive cell lines. From the clonal cells, adaptive mutations are then identified.

These adaptive mutations were located in NS3 (K272R), NS4A (K34R) or NS5A (S232I). Identification of these mutations suggests that these mutations contribute to the HCV's capability to replicate in cells in vitro, a phenomenon not observed with wild-type HCV genotype 6 RNA. Such contribution has then been confirmed by engineering the mutations, by site-directed mutagenesis, into genotype 6 RNA and introducing them into the cell lines. Genotype 6 HCV RNA, with such mutations, successfully replicated in the cell lines. Therefore, the Applicant has demonstrated that the Applicant has prepared HCV genotype 6 replicons capable of replication in vitro and has identified adaptive mutations leading to such capabilities.

Accordingly, in one embodiment, the present disclosure provides a genotype 6 hepatitis C viral (HCV) RNA that is capable of replication in a host cell. In one aspect, the replication is in vitro. In another aspect, the replication is productive. In another aspect, the cell is a eukaryotic cell such as a mammalian cell or a human cell. In yet another aspect, the cell is a hepatoma cell. In some aspects, the RNA can replicate to produce at least 10 copies of the RNA in a cell. In another aspect, the number of copies is at least about 100, 500, 1000, 2000, 5000, 10,000, $1\times10^5$, $1\times10^6$, $1\times10^7$, $1\times10^8$ or $1\times10^9$.

The HCV RNA can be a subgenomic HCV sequence. It is specifically contemplated that a full-length HCV replicon containing any or more of such adaptive mutations is also capable to replicate. Still further, an entire HCV virus of the corresponding genotype containing the adaptive mutation(s) would be infectious and capable to replicate. In any such case, RNA can include one or more of 5'UTR, optionally an internal ribosome entry site (IRES), sequences encoding NS3, NS4A, NS4B, NS5A and NS5B, and a 3'NTR. In one aspect, the RNA includes, from 5' to 3' on the positive-sense nucleic acid, a functional HCV 5' non-translated region (5'NTR) or untranslated region (5'UTR) comprising an extreme 5'-terminal conserved sequence; an HCV polyprotein coding region;

and a functional HCV 3' non-translated region (3'NTR) or untranslated region (3'UTR) comprising an extreme 3'-terminal conserved sequence.

In one embodiment, a genotype 6 HCV RNA construct is capable of replication in a eukaryotic cell. The RNA sequence comprises a 5'UTR, sequences encoding one or more of NS3, NS4A, NS4B, NS5A or NS5B, and a 3'NTR. The RNA construct contains an adaptive mutation in NS3, NS4A, NS4B, NS5A or NS5B as compared to the wildtype.

In any of the above embodiments, the HCV RNA can include an adaptive mutation that enables the RNA to replicate in the cell. Such adaptive mutations, in NSA5 can include an isoleucine at residue 232.

Non-limiting examples of adaptive mutation for genotype 6 also include a mutation to arginine at residue 272 in NS3, and/or a mutation to arginine at residue 34 in NS4A.

In one embodiment, provided are replicons having one or more mutations listed in Table 2. In one aspect, the HCV RNA includes at least an adaptive mutation in NS3 and at least an adaptive mutation in NS4A. In another aspect, the HCV RNA includes at least an adaptive mutation in NS3 and at least an adaptive mutation in NS5A. In yet another aspect, the HCV RNA includes at least an adaptive mutation in NS4A and at least an adaptive mutation in NS5A.

Also contemplated are that the HCV RNA can be a RNA sequence that has at least about 75%, or about 80%, 85%, 90%, 95%, 98%, 99%, or about 99.5% sequence identity to any of the disclosed sequences, so long as it retains the corresponding adaptive mutation(s) and/or activities.

Thus, in one aspect, a genotype 6 HCV RNA construct is provided, comprising a 5'UTR, sequences encoding NS3, NS4A, NS4B, NS5A and NS5B, and a 3'UTR, wherein the construct is capable to replicate in a eukaryotic cell. In one aspect, the construct comprises an adaptive mutation in NS3, NS4A, NS4B, NS5A or NS5B.

In one aspect, the construct include one, two or three of the discovered adaptive mutations. In some aspect, the genotype 6 is genotype 6a.

In any of the above embodiments, the HCV RNA can further comprise a marker gene for selection. A non-limiting example of such a marker gene is a neomycin phosphotransferase gene. Other examples are well known in the art.

In any of the above embodiments, the HCV RNA can further comprise a reporter gene. A non-limiting example of such marker gene is a luciferase gene, such as Rluc reporter gene. Other examples are well known in the art.

The RNA construct of any of the above embodiment can further comprise sequences encoding one or more of C, E1 or E2. In one aspect, the RNA construct is a full-length HCV replicon.

The disclosure also provides a single or double-stranded DNA that can be transcribed to a RNA construct of any of the above embodiment, a viral particle comprising a RNA construct of any of the above embodiment, or an isolated cell comprising a RNA construct of any of the above embodiment.

In one embodiment, the present disclosure provides an NS3 protein of HCV genotype 6 that comprises an arginine at residue 272 (K272R).

In one embodiment, the present disclosure provides an NS4A protein of HCV genotype 6 that comprises an arginine at residue 34 (K34R).

In one embodiment, the present disclosure provides an NS5A protein of HCV genotype 6 that comprises an isoleucine at residue 232 (S232I).

In one aspect of any such embodiments, the genotype 6 is genotype 6a. In yet another aspect, provided is a polynucleotide encoding the protein of any of such embodiments. The polynucleotide can be RNA or DNA. In another aspect, provided is an RNA or DNA construct comprising the polynucleotide. In yet another aspect, provided is a cell comprising the polynucleotide. Still in one aspect, provided is an antibody that specifically recognizes a protein of any of the above embodiments.

Also provided are polynucleotide primers, probes or amplification products that specifically hybridize to the construct or the DNA encoding it, with one or more of the adaptive mutations, wherein the primers, probes or amplification products are at least 15 nucleotides long. In some aspects, the minimum length is 16, 17, 18, 19, 20, 21, 22, 23, 24, 25 or 30 nucleotides long. Such polynucleotides are useful for detecting the presence of the adaptive mutations.

HCV Genotype 6 Replicons and Cells Containing the Replicons

Another embodiment of the present disclosure provides an isolated cell comprising a genotype 6 hepatitis C viral (HCV) RNA that replicates in the cell. In one aspect, there is an absence, in the cell, of a DNA construct encoding the RNA and thus copies of the HCV RNA are not transcribed from a DNA, such as cDNA, construct.

In one aspect, the cell comprises at least 10 copies of the RNA. In another aspect, the cell comprises at least 100, 500, 1000, 2000, 5000, 10,000, $1\times10^5$, $1\times10^6$, $1\times10^7$, $1\times10^8$ or $1\times10^9$ copies of the RNA.

The HCV RNA can be subgenomic HCV sequence or a full-length HCV sequence. In either case, RNA can include one or more of 5'NTR, sequences encoding NS3, NS4A, NS4B, NS5A and NS5B, and a 3'NTR.

In any of the above embodiments, the HCV RNA can include an adaptive mutation that enables the RNA to replicate in the cell. Such adaptive mutations can include an isoleucine at location 232 at NS5A.

Non-limiting examples of adaptive mutation for genotype 6 also include a mutation to arginine at residue 272 in NS3, and/or a mutation to arginine at residue 34 in NS4A.

In one embodiment, the adaptive mutation are provided in Table 2. In one aspect, the HCV RNA includes at least an adaptive mutation in NS3 and at least an adaptive mutation in NS4A. In another aspect, the HCV RNA includes at least an adaptive mutation in NS3 and at least an adaptive mutation in NS5A. In yet another aspect, the HCV RNA includes at least an adaptive mutation in NS4A and at least an adaptive mutation in NS5A.

Also contemplated are that the HCV RNA can be a RNA sequence that has at least about 75%, or about 80%, 85%, 90%, 95%, 98%, 99%, or about 99.5% sequence identity to any of the disclosed sequences, so long as it retains the corresponding adaptive mutation(s).

In one aspect, the cell is a eukaryotic cell such as a mammalian cell and in particular a human cell. In another aspect, the cell is hepatoma cell, such as but not limited to a Huh7 cell (e.g., Huh7-Lunet, 51C and 1C). It is herein discovered surprisingly that Huh7 1C cell is particularly permissive to the genotype 6 replicons and thus in one aspect, the cell is a Huh7 1C cell. In some aspects, the cell is placed at an in vitro or ex vivo condition.

Methods of Preparing Genotype 6 Replicons

After HCV genotype 6 replicons are identified, as shown in Example 1, introduction of the relevant adaptive mutation into a corresponding genotype HCV RNA can result in the RNA's capability to replicate, in particular in a mammalian cell in vitro. Accordingly, the present disclosure provides a method of improving the capability of a genotype 6 HCV viral RNA to replicate in a eukaryotic cell, comprising one or more of:

(a) substituting residue 232 of NS5A with an isoleucine,
(b) substituting residue 272 of NS3 with an arginine, or
(c) substituting residue 34 of NS4A, with an arginine. In one aspect, the method comprises at least two substitutions of (a)-(c).

In one embodiment, the method entails further introducing one, two, three, or more mutations listed in Table 2. In one aspect, the mutations introduced include at least an adaptive mutation in NS4A, at least an adaptive mutation in NS3, and or at least an adaptive mutation in NS5A. In yet another aspect, the mutations introduced include at least an adaptive mutation in NS4A and at least an adaptive mutation in NS5A.

Methods of Screening HCV Inhibitors Targeting Genotype 6

Numerous known and unknown HCV inhibitors have been tested for their efficiency in inhibiting the genotype 6 HCV, in comparison with genotype 1b (Example 1). Some showed higher efficacy for genotype 6, and some were not as efficacious. The usefulness of the new identified genotype 6 replicons, therefore, is adequately demonstrated.

Thus, the present disclosure also provides, in one embodiment, a method of identifying an agent that inhibits the replication or activity of a genotype 6 HCV, comprising contacting a cell of any embodiment of the present disclosure with a candidate agent, wherein a decrease of replication or a decrease of activity of a protein encoded by the RNA indicates that the agent inhibits the replication or activity of the HCV. In some aspects, the protein is a protease, such as any or more of NS3, NS4A, NS4B, NS5A or NS5B. Replication of the RNA, in one aspect, can be measured by a reporter gene on the RNA, such as the luciferase gene.

Provided in another embodiment is a method of identifying an agent that decreases or inhibits the activity of a genotype 6 HCV, comprising contacting the lysate of a cell of any embodiment of the present disclosure with a candidate agent, wherein a decrease of the activity of a protein encoded by the RNA indicates that the agent inhibits the activity of the HCV. In one aspect, the protein is a protease, such as any or more of NS3, NS4A, NS4B, NS5A or NS5B. In another aspect, the method further comprises measuring the replication of the RNA or the activity of the protein encoded by the RNA.

A HCV inhibitor (or "candidate agent") can be a small molecule drug that is an organic compound, a peptide or a protein such as antibodies, or nucleic acid-based such as siRNA. In May 2011, the Food and Drug Administration approved 2 drugs for Hepatitis C, boceprevir and telaprevir. Both drugs block an enzyme that helps the virus reproduce. Boceprevir is a protease inhibitor that binds to the HCV NS3 active site on hepatitis C genotype 1. Telaprevir inhibits the hepatitis C virus NS3.4A serine protease.

More conventional HCV treatment includes a combination of pegylated interferon-alpha-2a or pegylated interferon-alpha-2b (brand names Pegasys or PEG-Intron) and the antiviral drug ribavirin. Pegylated interferon-alpha-2a plus ribavirin may increase sustained virological response among patients with chronic hepatitis C as compared to pegylated interferon-alpha-2b plus ribavirin according to a systematic review of randomized controlled trials.

All of these HCV inhibitors, as well as any other candidate agents, can be tested with the disclosed methods for their efficacy in inhibiting HCV genotype 6. The cells are then incubated at a suitable temperature for a period time to allow the replicons to replicate in the cells. The replicons can include a reporter gene such as luciferase and in such a case, at the end of the incubation period, the cells are assayed for luciferase activity as markers for replicon levels. Luciferase expression can be quantified using a commercial luciferase assay.

Alternately, efficacy of the HCV inhibitor can be measured by the expression or activity of the proteins encoded by the replicons. One example of such proteins is the NS3 protease, and detection of the protein expression or activity can be carried out with methods known in the art, e.g., Cheng et al., *Antimicrob Agents Chemother* 55:2197-205 (2011).

Luciferase or NS3 protease activity level is then converted into percentages relative to the levels in the controls which can be untreated or treated with an agent having known activity in inhibiting the HCV. A decrease in HCV replication or decrease in NS3 activity, as compared to an untreated control, indicates that the candidate agent is capable of inhibiting the corresponding genotype of the HCV. Likewise, a larger decrease in HCV replication or larger decrease in NS3 activity, as compared to a control agent, indicates that the candidate is more efficacious than the control agent.

EXAMPLES

The present disclosure is further defined by reference to the following examples. It will be apparent to those skilled in the art that many modifications, both to compositions and methods, may be practiced without departing from the scope of the current disclosure.

ABBREVIATIONS

Unless otherwise stated all temperatures are in degrees Celsius (° C.). Also, in these examples and elsewhere, abbreviations have the following meanings:

| | |
|---|---|
| µF = | MicroFaraday |
| µg = | Microgram |
| µL = | Microliter |
| µM = | Micromolar |
| g = | Gram |
| hr = | Hour |
| mg = | Milligram |
| mL = | Milliliter |
| mM = | Millimolar |
| mmol = | Millimole |
| nM = | Nanomolar |
| nm = | Nanometer |
| pg = | pictograms |
| CDR = | complementary determining region |
| DMEM = | Dulbecco's modified Eagle's medium |
| EMCV = | encephalomyocarditis virus |
| FBS = | fetal bovine serum |
| FR = | framework region |
| HCV = | Hepatitis C virus |
| IRES = | internal ribosome entry site |
| NTR = | non-translated region |
| PCR = | polymerase chain reaction |
| PegIFN = | pegylated interferon |
| RBV = | ribavirin |
| rpm = | revolutions per minute |
| RT-PCR = | reverse transcription-polymerase chain reaction |
| UTR = | untranslated region |

Example 1

Generation of Robust Genotype 6 Hepatitis C Virus Subgenomic Replicons

This example shows that adaptive mutations were identified from genotype 6 HCV viral replicons capable of replication in Huh7 cells and that HCV replicons with these adaptive mutations are useful tools for antiviral drug screening.

Materials and Methods

Cell Culture.

Huh7-Lunet cells were obtained from ReBLikon GmbH (Mainz, Germany). 51C cells were derived by curing a Huh-7 Lunet-based genotype 1a replicon clone and were described previously (Robinson M. et al., *Antimicrob Agents Chemother* 2010; 54:3099-106). 1C cells were derived by curing a Compound B-resistant genotype 1a replicon clone derived from 51C cells, and showed much higher permissiveness to genotype 1a replicon replication.[24] All cell lines were propagated in Dulbecco's modified Eagle's medium (DMEM) as described previously (Cheng G. et al. *Antimicrob Agents Chemother* 2011; 55:2197-205.). Replicon cell lines were selected and maintained in complete DMEM containing 0.25 to 0.5 mg/ml G418 (Geneticin; Invitrogen).

Construction of Plasmids Encoding Genotype 6a HCV Subgenomic Replicons.

A plasmid (pGT6aNeoSG) encoding a subgenomic genotype 6a replicon based on the consensus sequence (SEQ ID NO: 1) (FIG. 1) of sixteen genotype 6a genomes available in the European HCV database (Table 1), was prepared by DNA synthesis and cloning (GeneScript, Piscataway, N.J.). The synthesized replicon incorporated following elements from 5' to 3' (FIG. 2A-C): (1) the genotype 6a consensus 5'UTR (342 nt), plus the first 48 nucleotides of core, (2) a linker with the nucleotide sequence 5'-GGCGCGCCCA-3' (SEQ ID NO: 2), which introduces the AscI restriction site (underlined), (3) the neomycin phosphotransferase II (neo) gene, (4) a linker with nucleotide sequence 5'-GGCCGGCCA-3' (SEQ ID NO: 3), which introduces the FseI restriction site (underlined), (5) the encephalomyocarditis virus (EMCV) IRES, (6) a linker with nucleotide sequence 5'-ACGCGTATG-3' (SEQ ID NO: 4), which introduces the MluI restriction site (underlined) and an ATG start codon for HCV polyprotein expression, (7) the NS3-NS5B polyprotein region of genotype 6a consensus sequence including an NS5A adaptive mutation S232I, and (8) the 3'-UTR of genotype 2a JFH-1 (239 nt; no genotype 6a 3'-UTR available). The synthetic DNA fragment encoding the genotype 6a replicon was inserted into pUC57 between EcoRI and XbaI restriction sites.

TABLE 1

List of sixteen genotype 6a genomes available in the European HCV database.

| Accession # | Virus Isolate | Sequence Length | Note |
| --- | --- | --- | --- |
| AY859526 | 6a33 | 9355 | Complete coding sequence; no 3'-UTR |
| DQ480512 | 6a77 | 9358 | Complete coding sequence; no 3'-UTR |
| DQ480513 | 6a35 | 9358 | Complete coding sequence; no 3'-UTR |
| DQ480514 | 6a63 | 9358 | Complete coding sequence; no 3'-UTR |
| DQ480515 | 6a64 | 9358 | Complete coding sequence; no 3'-UTR |
| DQ480516 | 6a61 | 9358 | Complete coding sequence; no 3'-UTR |
| DQ480517 | 6a73 | 9358 | Complete coding sequence; no 3'-UTR |
| DQ480518 | 6a65 | 9358 | Complete coding sequence; no 3'-UTR |
| DQ480519 | 6a66 | 9358 | Complete coding sequence; no 3'-UTR |
| DQ480520 | 6a67 | 9358 | Complete coding sequence; no 3'-UTR |
| DQ480521 | 6a69 | 9358 | Complete coding sequence; no 3'-UTR |
| DQ480522 | 6a72 | 9358 | Complete coding sequence; no 3'-UTR |
| DQ480523 | 6a62 | 9358 | Complete coding sequence; no 3'-UTR |
| DQ480524 | 6a74 | 9361 | Complete coding sequence; no 3'-UTR |
| EU246930 | D9 | 9376 | Complete coding sequence; no 3'-UTR |
| Y12083 | EUHK2 | 9340 | Complete coding sequence; no 3'-UTR |

The consensus sequence was generated using Vector NTi software (Invitrogen)

A second plasmid (pGT6aRlucNeoSG) encoding a subgenomic replicon that incorporated the humanized Renilla luciferase (hRluc) reporter gene was generated as follows: The pGT6aNeoSG plasmid (described above) was cut using AscI and MluI restriction enzymes (to remove the neo gene) and gel purified using a commercial kit (Qiagen, Valencia, Calif.). A gene fragment encoding the hRluc gene fused with the neo gene along with the EMCV region from phRlucNeoSG2a plasmid (described below) were PCR amplified using Accuprime super mix I (Invitrogen) with the following primers: 2aRlucNeoAscIFor: 5'-AAC ACC ATC GGCGCGCCC ATG GCT TCC AAG GTG TAC GAC-3' (AscI site is introduced by the primer and is underlined, SEQ ID NO: 5), 2aEMCVIRESMluIRev: 5'-TCGGGG CCA T ACGCGTAT CGT GTT TTT CAA AGG-3' (MluI site underlined, SEQ ID NO: 6). The subsequent PCR fragment was cut with AscI and MluI and gel purified using a commercial kit (Qiagen). The vector and insert pieces were ligated using the LigaFast Rapid DNA Ligation System per the manufacturer's protocol (Promega, Madison, Wis.). The resulting vector, pGT6aRlucNeoSG, was sequenced to confirm the correct orientation and sequence of the hRluc-Neo. The phRlucNeoSG2a plasmid was constructed by replacing the Luc-Neo fragment in the plasmid pLucNeoSG2a with the hRluc-Neo gene amplified from the plasmid hRluc-Neo Flexi® (Promega) as previously described (Robinson M. et al. *Antimicrob Agents Chemother* 2010; 54:3099-106; Cheng G. et al., *Antimicrob Agents Chemother* 2011; 55:2197-205).

A third plasmid (Pi-GT6aRlucSG), encoding a bicistronic replicon with the hRluc reporter gene downstream of the poliovirus IRES (PI) and the genotype 6a consensus HCV nonstructural genes (NS3-NS5B) downstream of the EMCV IRES was used for transient transfection studies. The plasmid was generated as follows: The pGT6aRlucNeoSG plasmid (described above) was cut using AscI and MluI restriction enzymes (to remove the Rluc-Neo gene) and gel purified using a commercial kit (Qiagen). A gene fragment encoding the PI, hRluc gene and EMCV region was PCR amplified from a genotype 1b Pi-Rluc plasmid using Accuprime super mix I (Invitrogen) with the following primers: 6aPiRlucAscIFor: 5'-AAC ACC ATC GGCGCGCCA AAC CAA GTT CAA TAG-3' (AscI site is introduced by the primer and is underlined, SEQ ID NO: 7), 1bEMCVIRESMluIRev: 5'-TCG GGG CCA TACGCGTAT CGT GTT TTT CAA AGG-3' (MluI site underlined, SEQ ID NO: 8). The subsequent PCR fragment was cloned and ligated as described above to generate the resulting vector, Pi-GT6aRlucSG.

Construction of Mutant Replicons.

Adaptive mutations were introduced into the pGT6aNeoSG, pGT6aRlucNeoSG or Pi-GT6aRlucSG replicons by site-directed mutagenesis using a QuikChange Lightening kit (Stratagene, La Jolla, Calif.). All mutations were confirmed by DNA sequencing by Elim Biopharm (Hayward, Calif.).

RNA Transcription.

Plasmids encoding genotype 6a subgenomic HCV replicons were linearized with XbaI and purified using a PCR purification kit (Qiagen). RNA was synthesized and purified with T7 MEGAScript (Ambion, Austin, Tex.) and RNeasy kits (Qiagen), respectively, according to the manufacturer's instructions. RNA concentrations were measured using optical density at 260 nm and confirmed by 0.8% agarose gel electrophoresis (Invitrogen).

RNA Transfection and Isolation of Stable Replicon Cell Lines.

Ten micrograms of in vitro-transcribed RNA were transfected into Huh7 Lunet or 1C cells by electroporation. Briefly, cells were collected by trypsinization and centrifugation, then washed twice with ice-cold phosphate buffered saline (PBS) and resuspended in Opti-MEM medium (Invitrogen) at a concentration of $10^7$ cells/ml. Replicon RNA was added to 400 µl of cell suspension in a Gene Pulser (BioRad, Hercules, Calif.) cuvette (0.4-cm gap). Cells were electroporated at 270 V and 960 µF, incubated at room temperature for 10 minutes, resuspended in 30 ml complete DMEM and then plated into two 100-mm-diameter dishes. Forty-eight hours after plating, medium was replaced with complete DMEM supplemented with 0.25 mg/ml G418, which was refreshed twice per week. After three weeks, cell clones were isolated, expanded with 0.5 mg/ml G418, and cryopreserved at early passages.

Replicon Colony Formation Assays.

To determine the efficiency of G418-resistant colony formation, cells were electroporated with the indicated amounts of replicon RNA or extracted cellular RNA, and plated at multiple densities ranging from $2 \times 10^5$ to $2 \times 10^6$ cells/100-mm dish. Forty-eight hours after plating, media were replaced with complete DMEM supplemented with 0.5 mg/ml G418, which was refreshed twice per week. Three weeks later, colony plates were used for cell expansion or G418-resistant foci were fixed with 4% formaldehyde and stained with 0.05% crystal violet.

Extraction, Amplification, and Genotypic Analysis of HCV RNA.

HCV RNA isolation, RT-PCR, and population sequencing were performed as described previously (Cheng G. et al., *Antimicrob Agents Chemother* 2011; 55:2197-205). Briefly, HCV replicon cellular RNA were extracted and purified using an RNeasy kit (Qiagen) according to the manufacturer's protocol. RT-PCR was performed using the SuperScript III first-strand synthesis system (Invitrogen), and PCR products were subsequently sequenced by Elim Biopharm (Hayward, Calif.).

Detection of NS5A Protein by Indirect Immunofluorescence.

Replicon cells were plated in 96-well plates at a density of $1 \times 10^4$ cells per well. After incubation for 24 hours, cells were then stained for NS5A protein as described previously (Cheng G. et al., *Antimicrob Agents Chemother* 2011; 55:2197-205). Briefly, cells were fixed in 4% paraformaldehyde for 20 minutes. Cells were then washed three times with PBS, blocked with 3% bovine serum albumin, 0.5% Triton X-100, and 10% FBS and stained with anti-NS5A antibody. Staining was performed using a 1:10,000 dilution of mouse monoclonal antibody 9E10 (Apath, Brooklyn, N.Y.). After washing in PBS three times, a secondary anti-mouse antibody conjugated to Alexa Fluor 555 was used to detect anti-NS5A antibody labeled cells (Invitrogen). Nuclei were stained with 1 µg/ml Hoechst 33342 (Invitrogen). Cells were washed with PBS and imaged with a Zeiss fluorescence microscope (Zeiss, Thornwood, N.Y.).

Replicon Antiviral Assays.

Replicon RNA were electroporated into 1C cells as described above. After transfection, cells were quickly transferred into 100 mL of pre-warmed culture medium, and 90 µl was seeded in 384-well plates at a density of 2,000 cells/well. Cells were treated with three-fold serial drug dilutions at 10 different concentrations. Cell plates were incubated at 37° C. for 3 days, after which culture medium was removed and cells were assayed for luciferase activity as markers for replicon levels. Luciferase expression was quantified using a commercial luciferase assay (Promega). Luciferase levels were converted into percentages relative to the levels in the untreated controls (defined as 100%), and data were fitted to the logistic dose-response equation $y=a/[1+(x/b)^c]$ using XLFit4 software (IDBS, Emeryville, Calif.).

Antiviral Compounds.

Telaprevir, boceprevir, and 2-C-methyl adenosine (2-CMeA) were purchased from Acme Bioscience (Belmont, Calif.). Cyclosporine A (CsA) was purchased from Sigma-Aldrich (St. Louis, Mo.). The Wyeth HCV NS5B site IV inhibitor HCV-796 was synthesized by Curragh Chemistries (Cleveland, Ohio). Gilead compounds Compound B, tegobuvir, Compound A, Compound C, and sofobusvir, Pfizer NS5B thumb site II inhibitor filibuvir, Merck NS5B thumb site I inhibitor MK-3281 and protease inhibitor MK-5172, and the Bristol-Myers Squibb NS5A inhibitor daclatasvir (BMS-790052) were synthesized by Gilead Sciences. The structures of the certain Gilead compounds are provided below:

Compound A

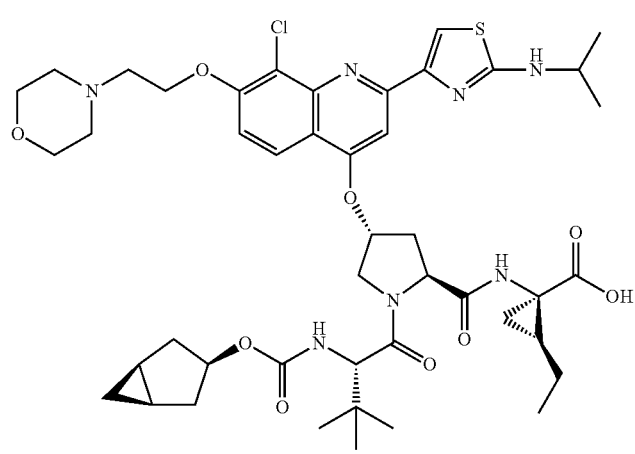

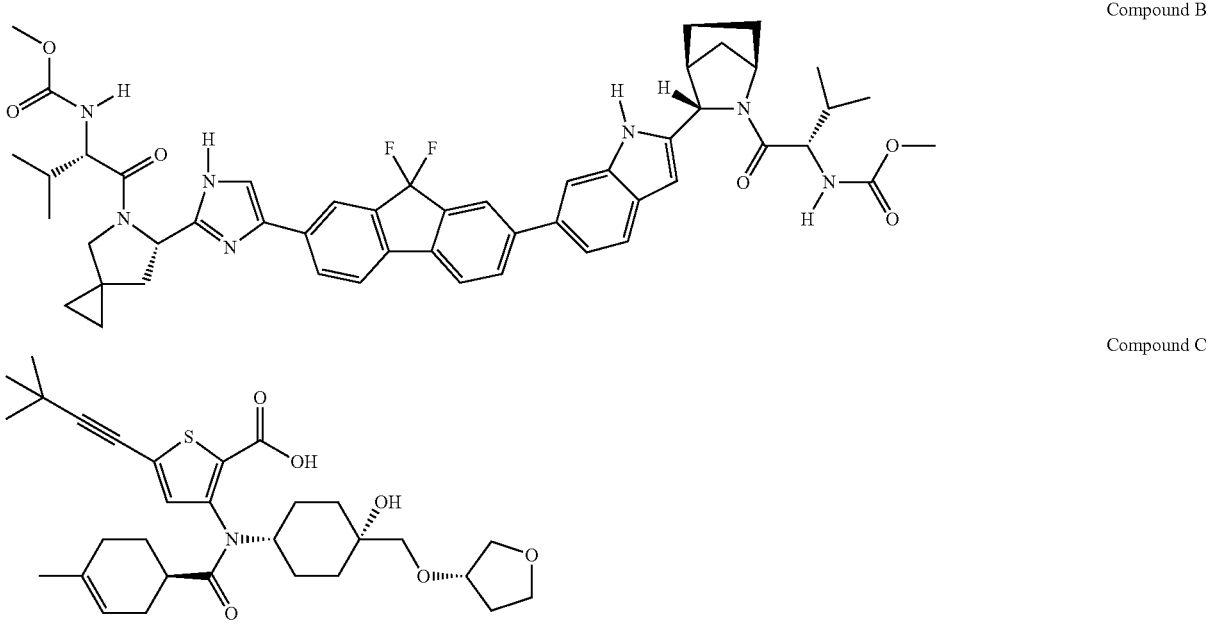

Compound B

Compound C

Results

Figure 3:
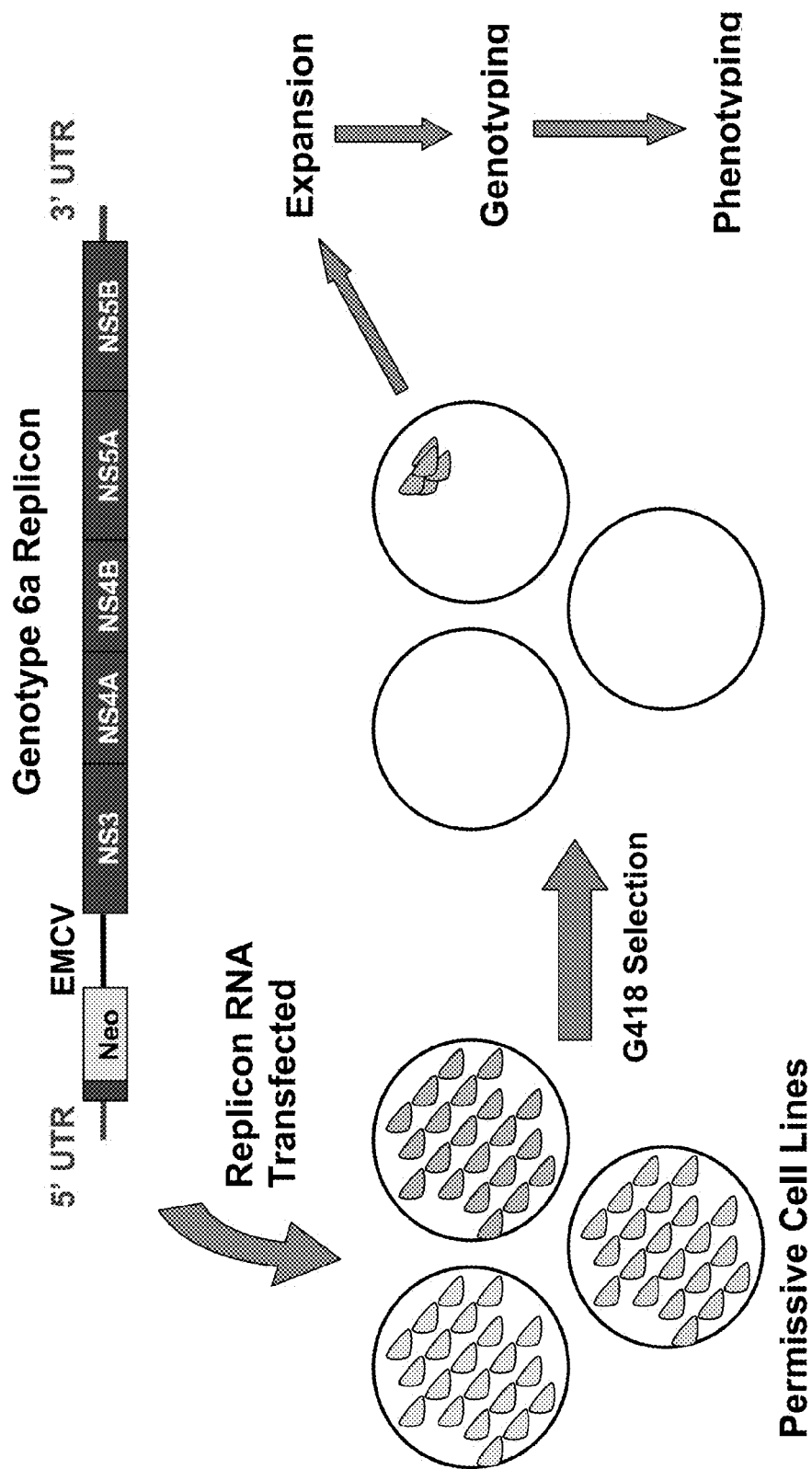
Figure 4:
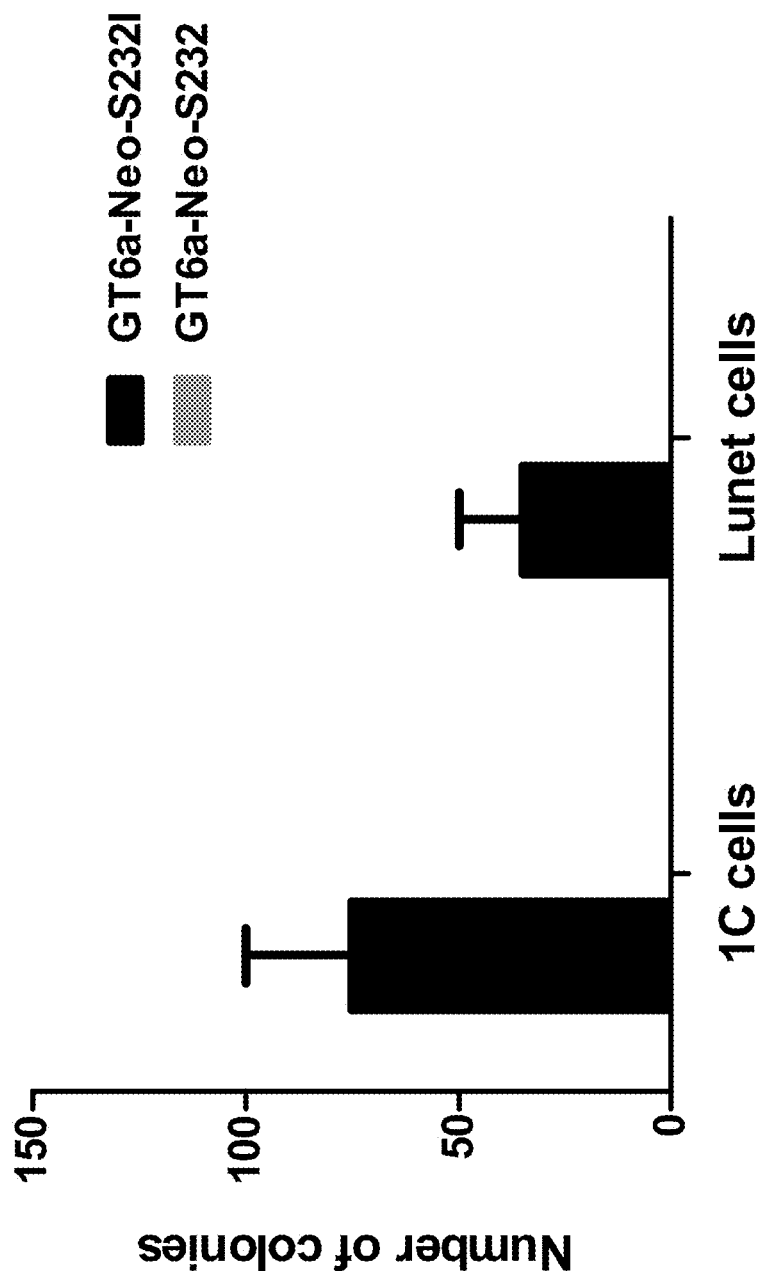
Figure 5:
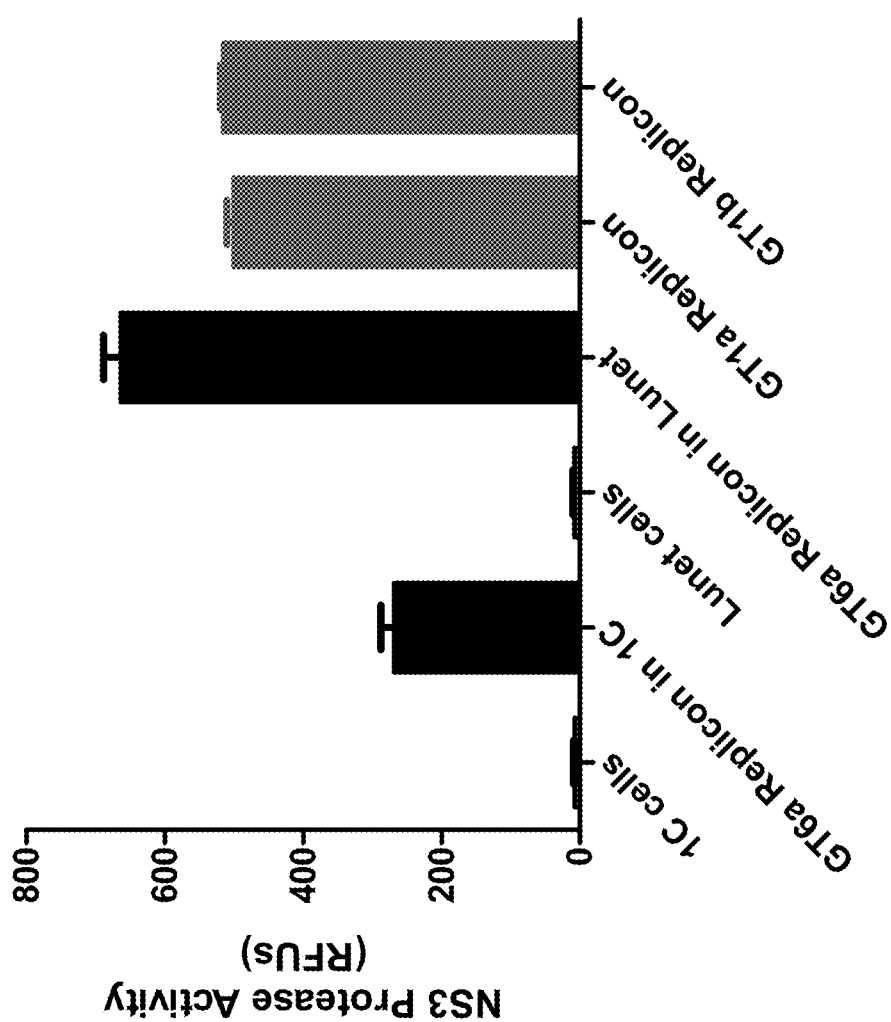
Figure 6:
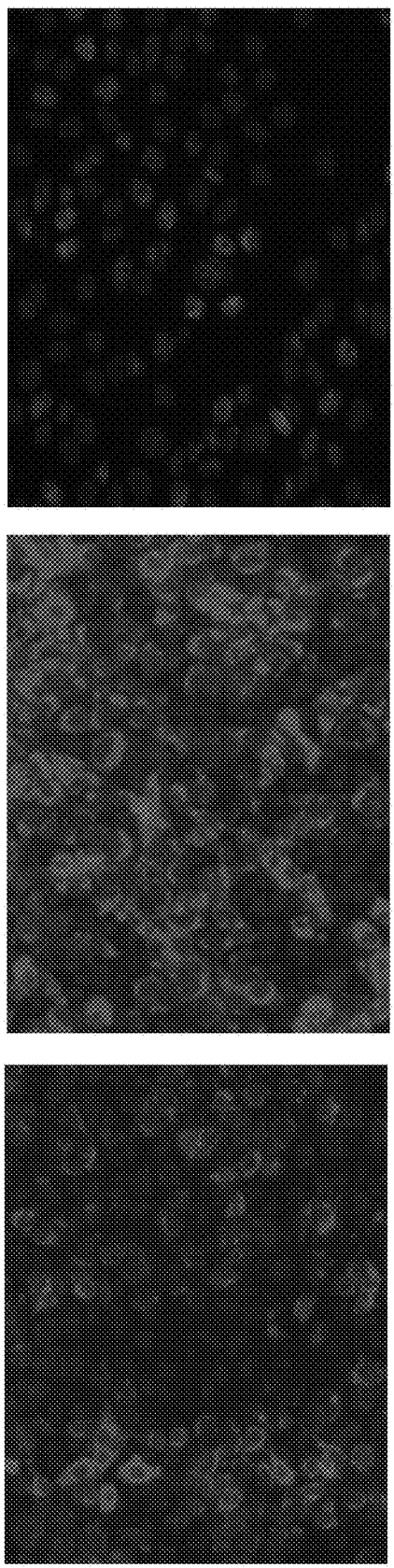

Transfection of the GT6a replicon into Huh7-Lunet cells yielded 35 stable replicon colonies (see illustrated replicon isolation strategy in FIG. 3), which all required NS5A S232I mutation. Genotypic analysis of replicon colonies revealed multiple new adaptive mutations. K272R (in NS3) and K34R (in NS4A) were observed most frequently and were confirmed to enhance GT6a replication.

Stable colony formation of genotype 6a replicons with NS5A mutation S232I was evident (FIG. 4). Transfection of the GT6aNeoSG replicon RNA (10 mg) with the NS5A mutation S232I into Huh-7 Lunet or 1C cells yielded 35 and 75 stable colonies respectively. However, in the absence of the S232I mutation, no replicon colonies survived in either cell line after multiple independent selections. These results suggest that although genotype 6a HCV has low replication efficiency in cell culture, stable replicon colonies could be selected and that the NS5A mutations S232I was required for colony formation. Eleven and thirteen replicon colonies were isolated and expanded from 1C and Lunet cells, respectively. The remaining colonies were pooled for genotypic and phenotypic characterization.

It was also observed that the replicons that harboring the adaptive mutation showed high NS3 protease activity (FIG. 5). Pooled GT6a replicon cells were seeded in 96-well plates at a concentration of $5\times10^4$ cells per well. After incubation for 24 hours, the replicon cells were then lysed with 90 μl of 1× Promega luciferase lysis buffer supplemented with 150 mM NaCl at room temperature for 20 min on a plate shaker. 10 μl of 1 μM europium-labeled NS3 substrate in the above lysis buffer was added to each well. Protease activity data were collected and analyzed. These results indicate that GT6a replicon cells have high levels of NS3 protease activity which are comparable to standard GT1a and GT1b replicon cells.

Further, these replicons exhibited high NS5A expression in GT6a replicon cells (FIG. 6). Pooled GT6a replicon cells were stained with anti-NS5A antibody (red, shown light gray) and Hoechst 33342 (blue, indicating nuclei, shown as dark gray). 1C cells were stained as a negative control. The results of immunohistochemical analysis confirmed the high expression level of NS5A protein, particularly in the perinuclear region.

Selected GT6a replicon clones or pooled cell lines were expanded and subjected to genotypic analysis. Total cellular RNA was extracted and purified using an RNeasy kit (Qiagen). RT-PCR was performed using the SuperScript III first-strand synthesis system (Invitrogen). PCR products were sequenced by Elim Biopharm. Only amino acid changes are indicated (Table 2). All clones or pools retained the NS5A mutation S232I. No major mutations were identified in the pooled cell lines from population sequencing; this is likely due to lack of a dominant mutation but the co-existence of multiple different adaptive mutations below the detection threshold for population sequencing.

TABLE 2

Adaptive mutations identified in GT6a replicon cells

| Cells | GT6a Clone# | NS3 | NS4A | NS5A | NS5B |
|---|---|---|---|---|---|
| 1C | 1 | K272R | | | |
| | 2 | | K34R | | |
| | 3 | K272R | | | |
| | 4 | D405Y | | L361P | |
| | 5 | K272R | | | |
| | 6 | E30V(E) | | | |
| | 7 | P89L | | | |
| | 8 | K272R | | | |
| | 9 | E110V | | | |
| | 10 | Q195P | | | |
| | 11 | K272R | | | |
| | Pool | — | — | — | — |
| Lunet | 1 | T580A/T621A(T) | | | |
| | 2 | | | | I11V |
| | 3 | T621A | | | |
| | 4 | T261P | | | |
| | 5 | T312P | | | |
| | 6 | | E52V | | |
| | 7 | | K34R | | |
| | 8 | T76I | | | |
| | 9 | | K34R | | |
| | 10 | E30V(E) | | | |

TABLE 2-continued

Adaptive mutations identified in GT6a replicon cells

| Cells | GT6a Clone# | NS3 | NS4A | NS5A | NS5B |
|---|---|---|---|---|---|
| | 11 | | | L31V | |
| | 12 | K272R | | | |
| | Pool | — | — | — | — |

Five mutations (Table 3) that either emerged independently at least twice (E30V and K272R in NS3 and K34R in NS4A) or corresponded to certain adaptive mutations identified in GT3a (e.g., P89L in NS3) or GT4a (E52V in NS4a) replicons, were chosen and introduced into GT6a-RlucNeo or Pi-GT6a-Rluc replicons (carrying S232I mutation in NS5A) individually by site-directed mutagenesis. All replicon RNAs were transfected into Lunet cells or 1C cells to determine whether they enhance GT6a HCV replication by colony formation assays with GT6a-RlucNeo replicons or luciferase activity measurement with Pi-GT6a-Rluc replicons.

TABLE 3

Mutations were analyzed for adaptive phenotype in GT6a Replicons

| Mutations | Number of appearances | Locations |
|---|---|---|
| K272R | 6 | NS3 |
| K34R | 3 | NS4A |
| E30V | 2 | NS3 |
| P89L | 1 | NS3 |
| E52V | 1 | NS4A |

Figure 7:
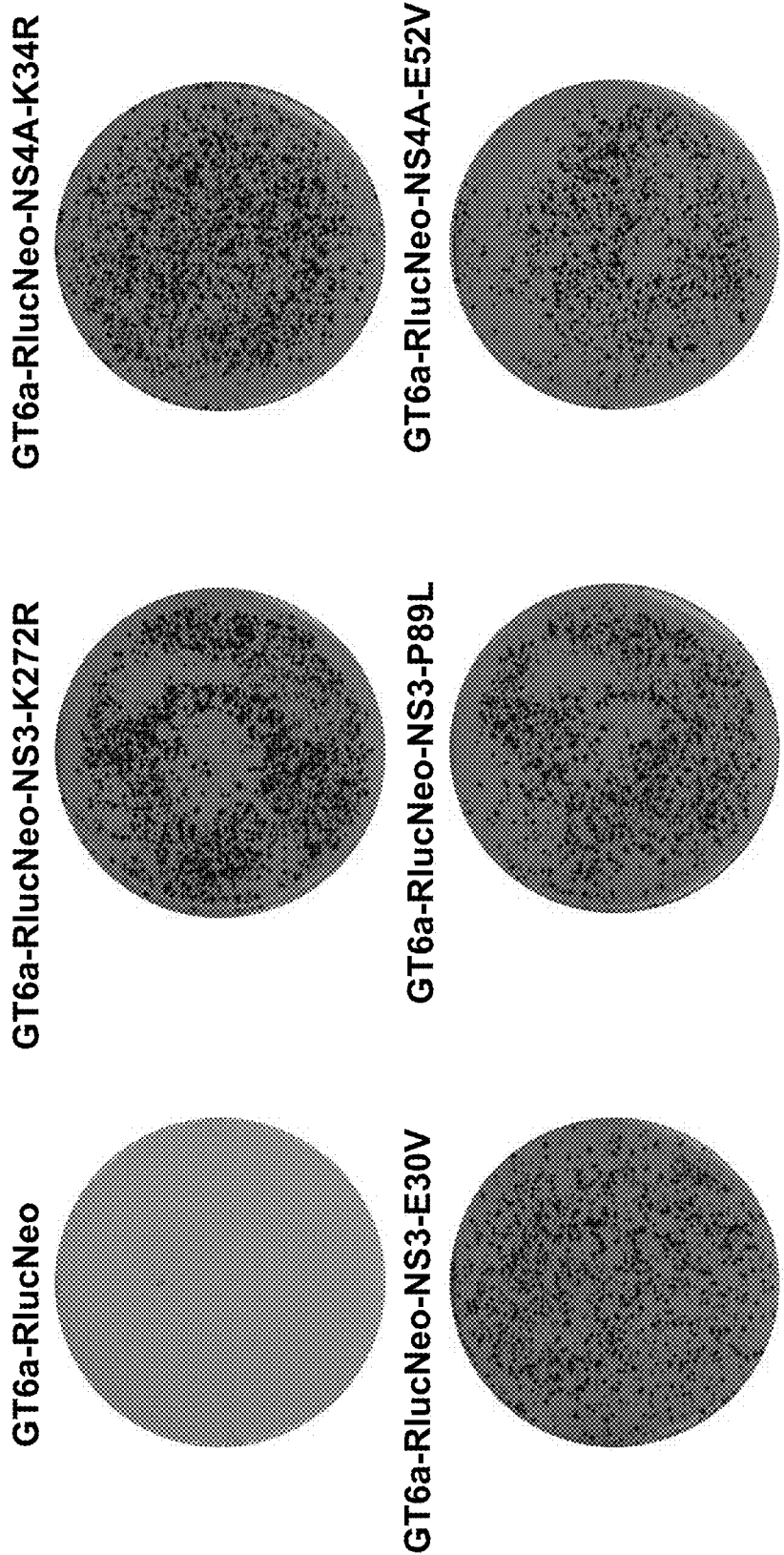

It was further shown that these NS3 and NS4A mutations enhanced GT6a replicon replication (FIG. 7). The NS3 mutations (E30V, P89L and K272R) and NS4A mutations (K34R and E52V mutations) were introduced into the GT6a-Rluc-Neo construct by site-directed mutagenesis. All replicon RNAs including the parental GT6a-RluNeo replicon (10 μg each; all carrying NS5A mutation S232I) were transfected into Lunet cells. Stable colony formation efficiency were assessed for each replicon. Replacement of Neo with RlucNeo resulted in significant reduction of stable colony formation (from 35 to 1 colonies) likely due to the larger size of RlucNeo reporter. Importantly, all 5 mutations either in NS3 or NS4A significantly enhanced GT6a HCV replication as evidenced by the large number of stable colonies emerging from replicons with any of the five mutations, compared to only 1 colony with the parental replicon.

Figure 8:
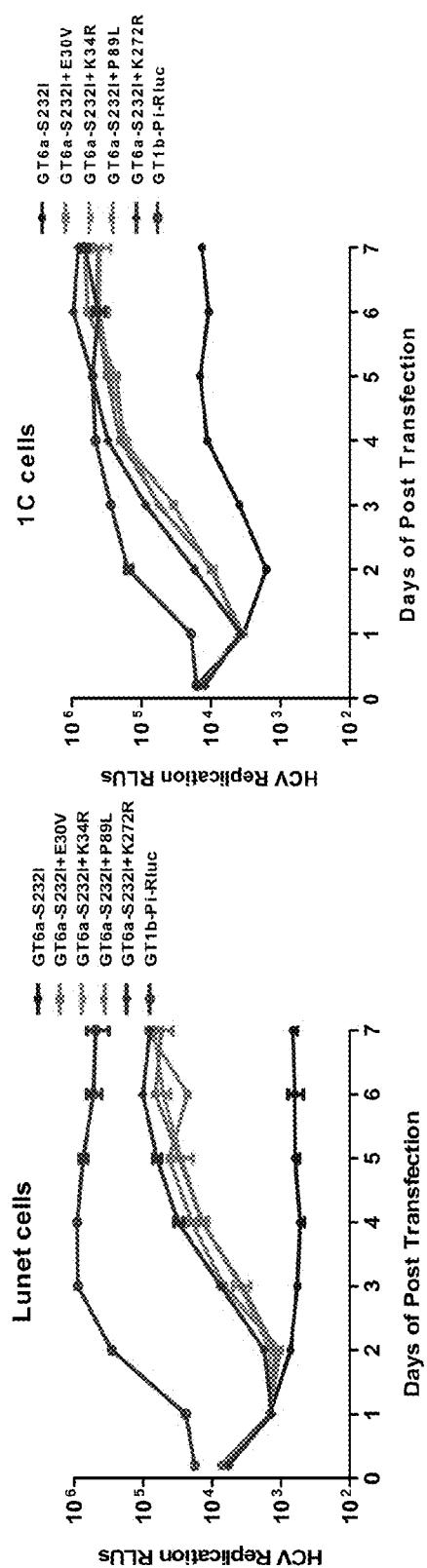

One interesting observation was that NS3 and NS4A mutations conferred high GT6a HCV replication and 1C are more permissive than Lunet cells (FIG. 8). To better quantify the enhancement of GT6a HCV replication, the NS3 mutations (E30V, P89L and K272R) and NS4A mutation K34R were introduced into the Pi-GT6a-Rluc construct by site-directed mutagenesis. All replicon RNAs including the parental GT6a-RluNeo replicon (10 mg each; all carrying NS5A mutation S232I) were transfected into Huh-7 Lunet or 1C cells respectively. An adapted Pi-GT1b-Rluc replicon was transfected in parallel for comparison. $5\times10^3$ transfected cells were plated into wells in a 96-well plate. At 4 hours and daily from day 1 to day 7 post transfection, cells were analyzed for renilla luciferase activity. In both Huh-7 Lunet and 1C cells, all mutations either in NS3 or NS4A significantly enhanced GT6a HCV replication as evidenced by much higher (>20-fold) luciferase activity of those replicons than the parental one. Furthermore, 1C cells were more permissive than Lunet cells. In Lunet cells, the replicons with adaptive mutations reached a peak luciferase activity of $1\times10^5$ RLUs, approximately 10-fold lower than the levels reached by GT1b replicons. In 1C cells, however, the peak luciferase activity was $1\times10^6$ RLUs which was comparable to levels reached by the highly adapted GT1b replicon.

Figure 9:
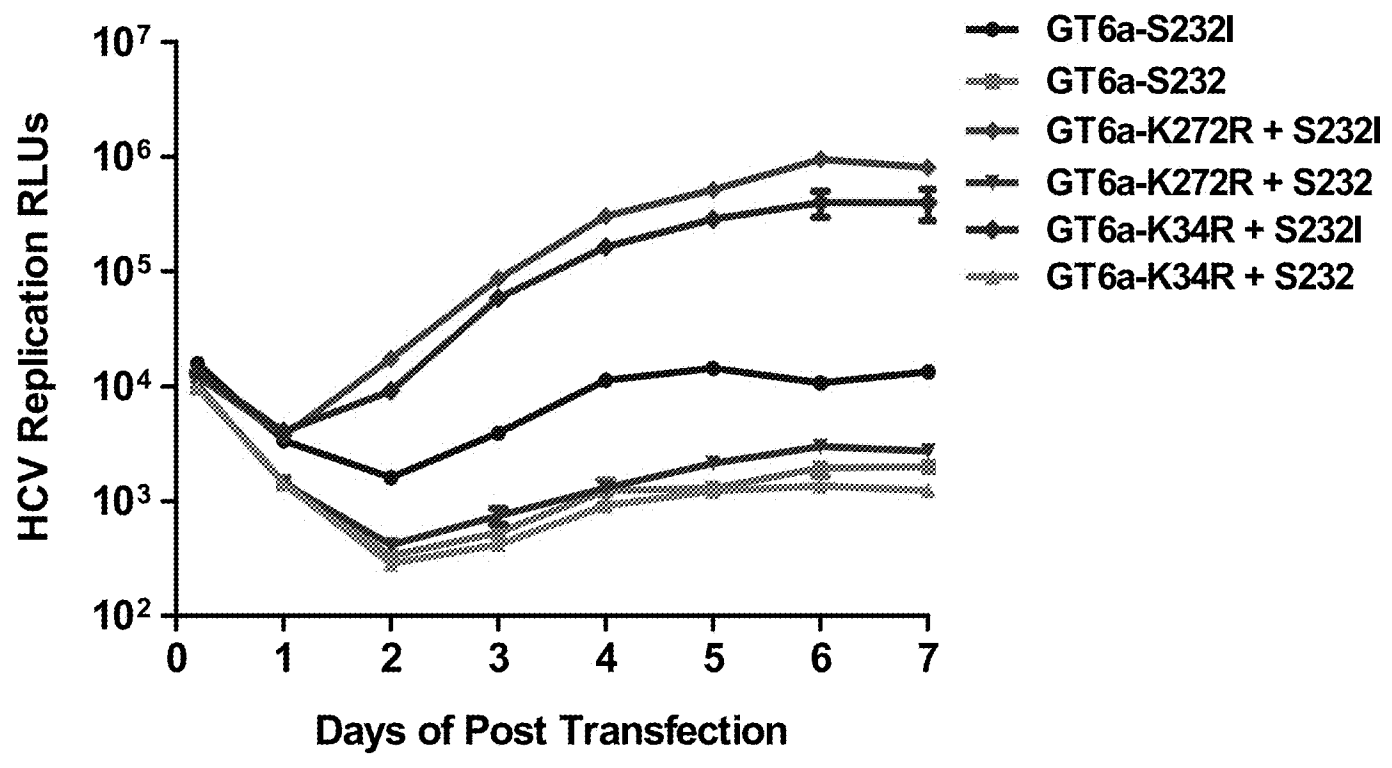

NS3 and NS4A adaptive mutations appeared to need the NS5A mutation S232I to confer efficient GT6a HCV replication (FIG. 9). To confirm whether the NS5A mutation S232I is required for the adaptive functions of the NS3 or NS4A mutations, the parental Pi-GT6a-Rlucreplicon or the replicon constructs carrying adaptive mutations K272R in NS3 or K34R in NS4A (all carrying the NS5A mutation S232I) were subjected to reversion of the S232I mutation to wile-type by site-directed mutagenesis. All replicon RNAs (10 mg each) were transfected into 1C cells individually and $5\times10^3$ transfected cells were plated into wells in a 96-well plate. At 4 hours and daily from day 1 to day 7 post transfection, cells were analyzed for luciferase activity. In the absence of mutation S232I, all replicons had significantly reduced their replication efficiency regardless of the presence of the NS3 mutation K272R or the NS4A mutations K34R. These results confirm that the NS3 and NS4A adaptive mutations require the NS5A mutation S232I to confer efficient GT6a HCV replication. Similar results were also observed in Lunet cells.

These new adaptive mutations allowed establishment of robust luciferase-encoding GT6a replicons for reproducible quantification of HCV replication, enabling determination of $EC_{50}$ values for five classes of HCV inhibitors in a 384-well format. While nucleos/tide NS5B inhibitors including sofosbuvir, cyclosporine A inhibitors and a majority of NS3 protease inhibitors had similar antiviral activity against both GT6a and GT1b, only some NS5A inhibitors (daclatasvir) and few non-nucleoside NS5B inhibitors (HCV-796) retained activity against GT6a (Table 4).

TABLE 4

Antiviral activity of various anti-HCV agents against both GT6a and GT1b

| Class | Compound | GT1b EC50 (nM) | GT6a EC50 (nM) | GT6a/GT1b EC50 ratio |
|---|---|---|---|---|
| NS5B NI | Sofosbuvir | 39 ± 1.1 | 14 ± 4.1 | 0.4 |
| | 2'C-MeA | 86 ± 0.1 | 23 ± 6.1 | 0.3 |
| NS3 PI | Telaprevir | 428 ± 22 | 349 ± 20 | 0.8 |
| | Boceprevir | 188 ± 42 | 177 ± 21 | 0.9 |
| | Compound A | 8.3 ± 1.6 | 72 ± 25 | 8.7 |
| | MK-5172 | 0.74 ± 0.07 | 2.3 ± 0.3 | 3.1 |
| NS5A inhibitor | Compound B | 0.007 ± 0.003 | 0.79 ± 0.05 | 113 |
| | Daclatasvir | 0.034 ± 0.018 | 0.06 ± 0.03 | 1.8 |
| NS5B NNI | Tegobuvir | 2.6 ± 0.2 | 119 ± 6 | 46 |
| | Filibuvir | 112 ± 13 | 3536 ± 93 | 32 |
| | Compound C | 3.5 ± 0.3 | 877 ± 4 | 251 |
| | HCV-796 | 20 ± 5.5 | 21 ± 0.5 | 1.0 |
| Host Target | Cyclosporin A | 81 ± 1.4 | 60 ± 2.7 | 0.8 |

Five different classes of HCV inhibitors as listed in the first column were evaluated for their antiviral activities against Pi-GT6a-Rluc and Pi-GT1b-Rluc replicons in a high throughput 384-well transient transfection assay, by measuring luciferase activity (Table 5). The data represents an average of at least two independent experiments with standard deviations.

TABLE 5

Antiviral activities of HCV inhibitors against genotype 1b and 6a replicons

| Inhibitor Classes | Compounds | GT6aRluc-K272R EC50 (nM) | GT6aRluc-K34R EC50 (nM) | GT1bRluc EC50 (nM) | GT6a(K272R)/1b EC50 ratio | GT6a(K34R)/1b EC50 Ratio |
|---|---|---|---|---|---|---|
| NS3 | Telaprevir | 208 ± 41 | 349 ± 20 | 428 ± 22 | 0.5 | 0.8 |
| Protease | Boceprevir | 185 ± 42 | 168 ± 21 | 181 ± 42 | 1 | 0.9 |
|  | Compound A | 67 ± 15 | 72 ± 25 | 8.3 ± 1.6 | 8.1 | 8.7 |
|  | MK-5172 | 3 ± 0.4 | 1.4 ± 0.3 | 0.74 ± 0.07 | 4.1 | 1.9 |
|  | BILN-2061 | 17 ± 1.6 | 17 ± 9 | 0.99 ± 0.1 | 17.2 | 17.2 |
| NS5A | Compound A | 0.95 ± 0.07 | 0.63 ± 0.03 | 0.007 ± 0.003 | 135.7 | 90 |
|  | BMS-790052 | 0.08 ± 0.04 | 0.04 ± 0.01 | 0.034 ± 0.018 | 2.4 | 1.2 |
| NS5B Nuc | Compound E | 14 ± 5 | 14 ± 4 | 39 ± 1.1 | 0.4 | 0.4 |
|  | 2-CMeA | 22 ± 8 | 23 ± 6 | 86 ± 0.1 | 0.3 | 0.3 |
| NS5B Non-Nuc | Compound C | 736 ± 18 | 877 ± 4 | 3.5 ± 0.3 | 210.3 | 250.6 |
|  | MK-3281 | 1311 ± 635 | 1276 ± 471 | 534 ± 47 | 2.5 | 2.4 |
|  | Compound D | 110 ± 21 | 119 ± 6 | 2.6 ± 0.2 | 42.3 | 45.8 |
|  | Filibuvir | 3536 ± 93 | >4444 | 112 ± 13 | 31.6 | >40 |
|  | HCV-796 | 21 ± 0.5 | 21 ± 0.5 | 20 ± 5.5 | 1.1 | 1.1 |
| Host Target | cyclosporin A | 65 ± 4.4 | 54 ± 1 | 81 ± 1.4 | 0.8 | 0.7 |

This example presents a robust GT6a replicon system established for in vitro antiviral screening. In conjunction with other genotype replicons this new reagent will aid in the development of pan-genotypic HCV regimens.

It will be appreciated that those skilled in the art will be able to devise various arrangements which, although not explicitly described or shown herein, embody the principles of the disclosure and are included within its spirit and scope. Furthermore, all conditional language recited herein is principally intended to aid the reader in understanding the principles of the disclosure and the concepts contributed by the inventors to furthering the art, and are to be construed as being without limitation to such specifically recited conditions. Moreover, all statements herein reciting principles, aspects, and embodiments of the disclosure are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

The invention claimed is:

1. A genotype 6 hepatitis C viral (HCV) RNA construct comprising a 5'UTR, sequences encoding NS4A, NS5A, and one or more of NS3, NS4B, or NS5B, and a 3'UTR, wherein the NS4A comprises a K34R mutation and the NS5A comprises an S232I mutation, each as compared to a wildtype genotype 6 HCV.

2. The RNA construct of claim 1, wherein the NS3, NS4A, NS4B or NS5B further comprises one or more mutations as compared to the wildtype.

3. The RNA construct of claim 2, wherein the NS3 comprises a K272R mutation as compared to the wildtype.

4. The RNA construct of claim 1, wherein the genotype 6 HCV is genotype 6a HCV.

5. The RNA construct of claim 1, further comprising a marker gene for selection.

6. The RNA construct of claim 5, wherein the marker gene is a neomycin phosphotransferase gene or a Rluc reporter gene.

7. The RNA construct of claim 1, wherein the construct comprises, from 5' to 3', the 5'UTR, sequences encoding NS3, NS4A, NS4B, NS5A and NS5B, and the 3'UTR.

8. An isolated cell comprising a RNA construct of claim 1.

9. An isolated cell comprising a genotype 6 hepatitis C viral (HCV) RNA that replicates in the cell, wherein the RNA comprises sequences encoding a NS4A protein comprising a K34R mutation and a NS5A protein comprising an S232I mutation, each of which mutations is as compared to a wild-type genotype 6 HCV.

10. The cell of claim 9, wherein there is an absence, in the cell, of a DNA construct encoding the RNA.

11. The cell of claim 9, wherein the cell comprises at least 10 copies of the RNA.

12. The cell of claim 9, wherein the RNA comprises a subgenomic HCV sequence.

13. The cell of claim 9, wherein the cell is a mammalian cell.

14. The cell of claim 13, wherein the cell is hepatoma cell.

15. The cell of claim 13, wherein the cell is a Huh7 1C cell.

16. The cell of claim 9, wherein the RNA comprises, from 5' to 3', the 5'UTR, sequences encoding NS3, NS4A, NS4B, NS5A and NS5B, and the 3'UTR.

17. The cell of claim 16, wherein the RNA further comprises a K272R mutation in NS3 protein compared to the wildtype.

* * * * *